(12) United States Patent
Novak et al.

(10) Patent No.: US 9,782,157 B2
(45) Date of Patent: *Oct. 10, 2017

(54) TISSUE RETRACTOR APPARATUS AND METHODS

(71) Applicant: Vycor Medical, Inc., Boca Raton, FL (US)

(72) Inventors: Theodore A. D. Novak, Boca Raton, FL (US); John Mangiardi, Greenwich, CT (US)

(73) Assignee: Vycor Medical, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,332

(22) Filed: Jan. 22, 2016

(65) Prior Publication Data

US 2016/0135800 A1    May 19, 2016

Related U.S. Application Data

(63) Continuation of application No. 13/674,507, filed on Nov. 12, 2012, now Pat. No. 9,307,969, which is a (Continued)

(51) Int. Cl.
  *A61B 17/02* (2006.01)
  *A61B 34/20* (2016.01)
  (Continued)

(52) U.S. Cl.
  CPC .......... *A61B 17/02* (2013.01); *A61B 1/00149* (2013.01); *A61B 1/32* (2013.01);
  (Continued)

(58) Field of Classification Search
  CPC ................ A61B 1/00149; A61B 1/32; A61B 2017/00022; A61B 2017/00057;
  (Continued)

(56) References Cited

U.S. PATENT DOCUMENTS 2,769,441 A    11/1956  Abramson
2,922,415 A     1/1960  Campagna
(Continued)

FOREIGN PATENT DOCUMENTS

CN    203724147     7/2014
DE    102005032197  1/2007
(Continued)

OTHER PUBLICATIONS

Alberti, O., et al., "Frameless navigation and endoscopy," Journal of Neurosurgery, Sep. 2001; 95(3): 541-3. Abstract only.
(Continued)

*Primary Examiner* — Pedro Philogene
(74) *Attorney, Agent, or Firm* — RatnerPrestia

(57) ABSTRACT

A delicate tissue retraction system having a hollow tubular retractor, a hollow tubular introducer that is removably installed within the retractor, and a navigation module that is removably installed within the introducer. The introducer has an inner passage defined by a passage wall having a width dimension that increases in size from a distal introducer end to a proximal introducer end. The navigation module has a shaft with a proximal shaft end, a middle shaft portion, and a distal shaft end, and a navigation unit mounted to the proximal shaft end. When assembled, the distal shaft end is contained generally within the introducer and the navigation module outside the introducer, and the middle shaft portion is spaced from the passage wall. The navigation module indicates the location of one or more points on at least one of the retractor and the introducer to a navigation system.

27 Claims, 13 Drawing Sheets

Related U.S. Application Data continuation of application No. 13/431,280, filed on Mar. 27, 2012, now abandoned, which is a continuation-in-part of application No. 12/545,686, filed on Aug. 21, 2009, now Pat. No. 8,608,650, which is a continuation of application No. 11/155,175, filed on Jun. 17, 2005, now abandoned.

(51) Int. Cl.
| | | |
|---|---|---|
| *A61B 1/32* | (2006.01) | |
| *A61B 1/00* | (2006.01) | |
| *A61M 25/01* | (2006.01) | |
| *A61B 17/34* | (2006.01) | |
| *A61B 17/00* | (2006.01) | |
| *A61B 90/57* | (2016.01) | |
| *A61B 90/10* | (2016.01) | |

(52) U.S. Cl.
CPC ...... *A61B 17/3421* (2013.01); *A61B 17/3439* (2013.01); *A61B 34/20* (2016.02); *A61M 25/0102* (2013.01); *A61B 17/3468* (2013.01); *A61B 90/10* (2016.02); *A61B 90/57* (2016.02); *A61B 2017/00022* (2013.01); *A61B 2017/00057* (2013.01); *A61B 2017/0212* (2013.01); *A61B 2017/3456* (2013.01)

(58) Field of Classification Search
CPC .... A61B 2017/0212; A61B 2017/3456; A61B 34/20; A61B 90/10; A61B 90/57; A61M 25/0102
USPC ........ 606/108, 191, 197, 199, 190; 600/114, 600/184, 201, 202, 215, 210; 604/164.01, 604/164.09, 164.1, 165.01, 165.02, 604/165.04, 166.01, 170.01, 170.02
See application file for complete search history.

(56) References Cited

U.S. PATENT DOCUMENTS

| | | | |
|---|---|---|---|
| 3,417,746 A * | 12/1968 | Moore | A61B 1/2676 348/359 |
| 3,608,547 A | 9/1971 | Sato | |
| 3,626,471 A | 12/1971 | Florin | |
| 3,690,323 A | 9/1972 | Wortman | |
| 3,766,910 A | 10/1973 | Lake | |
| 3,882,855 A | 5/1975 | Schulte | |
| 3,888,117 A | 6/1975 | Lewis | |
| 4,263,900 A | 4/1981 | Nicholson | |
| 4,312,353 A | 1/1982 | Shahbabian | |
| 4,386,602 A | 6/1983 | Sheldon | |
| 4,502,468 A | 3/1985 | Burgin | |
| 4,636,199 A | 1/1987 | Victor | |
| 4,638,798 A | 1/1987 | Shelden | |
| 4,931,039 A | 6/1990 | Coe | |
| 4,945,896 A | 8/1990 | Gade | |
| 5,052,373 A | 10/1991 | Michelson | |
| 5,135,526 A | 8/1992 | Zinnanti | |
| 5,160,323 A | 11/1992 | Andrew | |
| 5,183,464 A | 2/1993 | Dubrul | |
| 5,230,623 A | 7/1993 | Guthrie | |
| 5,249,568 A | 10/1993 | Brefka | |
| 5,251,127 A | 10/1993 | Raab | |
| 5,256,149 A | 10/1993 | Banik | |
| 5,271,380 A | 12/1993 | Riek | |
| 5,275,583 A | 1/1994 | Crainich | |
| 5,284,130 A | 2/1994 | Ratliff | |
| 5,305,203 A | 4/1994 | Raab | |
| 5,320,611 A | 6/1994 | Bonutti | |
| 5,334,150 A | 8/1994 | Kaali | |
| 5,356,421 A | 10/1994 | Castro | |
| 5,376,076 A | 12/1994 | Kaali | |
| 5,380,291 A | 1/1995 | Kaali | |
| 5,431,151 A | 7/1995 | Riek | |
| 5,431,676 A | 7/1995 | Dubrul | |
| 5,441,041 A | 8/1995 | Sauer | |
| 5,445,142 A | 8/1995 | Hassler, Jr. | |
| 5,467,762 A | 11/1995 | Sauer | |
| 5,513,238 A | 4/1996 | Leber | |
| 5,540,711 A | 7/1996 | Kieturakis | |
| 5,551,947 A | 9/1996 | Kaali | |
| 5,555,283 A | 9/1996 | Shiu | |
| 5,562,696 A | 10/1996 | Nobles | |
| 5,569,160 A | 10/1996 | Sauer | |
| D377,093 S | 12/1996 | Michelson | |
| 5,591,192 A | 1/1997 | Privitera | |
| 5,609,562 A | 3/1997 | Kaali | |
| 5,658,236 A | 8/1997 | Sauer | |
| 5,662,111 A | 9/1997 | Cosman | |
| 5,665,072 A | 9/1997 | Yoon | |
| 5,676,673 A | 10/1997 | Ferre | |
| 5,685,820 A | 11/1997 | Riek | |
| 5,702,761 A | 12/1997 | DiChiara, Jr. | |
| 5,738,628 A | 4/1998 | Sierocuk | |
| 5,748,703 A | 5/1998 | Cosman | |
| 5,748,767 A | 5/1998 | Raab | |
| 5,762,629 A | 6/1998 | Kambin | |
| 5,778,043 A | 7/1998 | Cosman | |
| 5,782,807 A | 7/1998 | Falvai | |
| 5,785,648 A | 7/1998 | Min | |
| 5,792,044 A | 8/1998 | Foley | |
| 5,800,352 A | 9/1998 | Ferre | |
| 5,803,089 A | 9/1998 | Ferre | |
| 5,829,444 A | 11/1998 | Ferre | |
| 5,848,967 A | 12/1998 | Cosman | |
| 5,860,996 A * | 1/1999 | Urban | A61B 17/3417 604/264 |
| 5,873,822 A | 2/1999 | Ferre | |
| 5,902,272 A | 5/1999 | Eggers | |
| 5,921,992 A | 7/1999 | Costales | |
| 5,947,981 A | 9/1999 | Cosman | |
| 5,967,970 A | 10/1999 | Cowan | |
| 5,967,980 A | 10/1999 | Ferre | |
| 5,971,997 A | 10/1999 | Guthrie | |
| 6,005,919 A | 12/1999 | Kooy | |
| 6,006,126 A | 12/1999 | Cosman | |
| 6,007,481 A | 12/1999 | Riek | |
| 6,041,101 A | 3/2000 | Kooy | |
| 6,047,218 A | 4/2000 | Whayne | |
| 6,083,191 A | 7/2000 | Rose | |
| 6,093,145 A | 7/2000 | VomBerg | |
| 6,096,038 A | 8/2000 | Michelson | |
| 6,120,465 A | 9/2000 | Guthrie | |
| 6,129,685 A | 10/2000 | Howard, III | |
| 6,142,931 A | 11/2000 | Kaji | |
| 6,156,054 A | 12/2000 | Zadno-Azizi | |
| 6,159,178 A * | 12/2000 | Sharkawy | A61B 17/3417 604/103.08 |
| 6,167,295 A | 12/2000 | Cosman | |
| 6,175,756 B1 | 1/2001 | Ferre | |
| 6,179,826 B1 | 1/2001 | Aebischer | |
| 6,214,017 B1 | 4/2001 | Stoddard | |
| 6,221,078 B1 | 4/2001 | Bylsma | |
| 6,224,599 B1 | 5/2001 | Baynham | |
| 6,228,059 B1 | 5/2001 | Astarita | |
| 6,236,875 B1 | 5/2001 | Bucholz | |
| 6,245,052 B1 | 6/2001 | Orth | |
| 6,256,859 B1 | 7/2001 | Stoddard | |
| 6,259,943 B1 | 7/2001 | Cosman | |
| 6,275,725 B1 | 8/2001 | Cosman | |
| 6,277,069 B1 | 8/2001 | Gray | |
| 6,278,766 B1 | 8/2001 | Kooy | |
| 6,283,912 B1 | 9/2001 | Hu | |
| 6,293,952 B1 | 9/2001 | Brosens | |
| 6,296,647 B1 | 10/2001 | Robioneck | |
| 6,326,875 B1 | 12/2001 | Tuovinen | |
| 6,331,180 B1 | 12/2001 | Cosman | |
| 6,341,231 B1 | 1/2002 | Ferre | |
| 6,351,661 B1 | 2/2002 | Cosman | |
| 6,359,959 B1 | 3/2002 | Butler | |
| 6,371,964 B1 | 4/2002 | Vargas | |
| 6,374,135 B1 | 4/2002 | Bucholz | |

(56) References Cited

U.S. PATENT DOCUMENTS

| | | |
|---|---|---|
| 6,383,191 B1 | 5/2002 | Zdeblick |
| 6,405,072 B1 | 6/2002 | Cosman |
| 6,409,686 B1 | 6/2002 | Guthrie |
| 6,416,520 B1 | 7/2002 | Kynast |
| 6,425,859 B1 | 7/2002 | Foley |
| 6,445,944 B1 | 9/2002 | Ostrovsky |
| 6,459,769 B1 | 10/2002 | Cosman |
| 6,461,330 B1 | 10/2002 | Miyagi |
| 6,478,028 B1 | 11/2002 | Paolitto |
| 6,478,806 B2 | 11/2002 | McFarlane |
| 6,551,240 B2 | 4/2003 | Henzler |
| 6,565,574 B2 | 5/2003 | Michelson |
| 6,589,211 B1 | 7/2003 | MacLeod |
| 6,595,917 B2 | 7/2003 | Nieto |
| 6,596,008 B1 | 7/2003 | Kambin |
| 6,599,292 B1 | 7/2003 | Ray |
| 6,602,227 B1 | 8/2003 | Cimino |
| 6,605,036 B1 | 8/2003 | Wild |
| 6,654,999 B2 | 12/2003 | Stoddard |
| 6,662,036 B2 | 12/2003 | Cosman |
| 6,669,685 B1 | 12/2003 | Rizoiu |
| 6,675,040 B1 | 1/2004 | Cosman |
| 6,685,630 B2 | 2/2004 | Sauer |
| 6,761,687 B1 * | 7/2004 | Doshi .............. A61B 1/303 600/184 |
| D495,053 S | 8/2004 | Laun |
| 6,863,674 B2 | 3/2005 | Kasahara |
| 6,896,680 B2 | 5/2005 | Michelson |
| 6,942,634 B2 | 9/2005 | Odland |
| 7,081,089 B2 | 7/2006 | Bonadio |
| 7,153,304 B2 | 12/2006 | Robie |
| 7,235,084 B2 | 6/2007 | Skakoon |
| 7,474,820 B2 | 1/2009 | Vayser |
| 7,510,524 B2 | 3/2009 | Vayser |
| 7,686,492 B2 | 3/2010 | Vayser |
| 8,360,970 B2 * | 1/2013 | Mangiardi .......... A61B 17/025 600/210 |
| 8,386,052 B2 | 2/2013 | Harris |
| 8,409,083 B2 | 4/2013 | Mangiardi |
| 8,608,650 B2 | 12/2013 | Mangiardi |
| 8,608,769 B2 | 12/2013 | Kahle |
| 8,679,088 B2 | 3/2014 | Abrahams |
| 9,216,015 B2 | 12/2015 | Wilson |
| 9,307,969 B2 * | 4/2016 | Novak ................. A61B 17/02 |
| 2001/0010002 A1 | 7/2001 | Michelson |
| 2001/0027271 A1 | 10/2001 | Franck |
| 2002/0022764 A1 | 2/2002 | Smith |
| 2002/0151769 A1 | 10/2002 | Kim |
| 2002/0161366 A1 | 10/2002 | Robie |
| 2003/0040753 A1 | 2/2003 | Daum |
| 2003/0073934 A1 | 4/2003 | Putz |
| 2003/0139648 A1 | 7/2003 | Foley |
| 2003/0145865 A1 | 8/2003 | Sterman |
| 2004/0024291 A1 | 2/2004 | Zinkel |
| 2004/0059375 A1 | 3/2004 | Ginn |
| 2004/0068172 A1 | 4/2004 | Nowinski |
| 2004/0097792 A1 | 5/2004 | Moll |
| 2004/0102804 A1 | 5/2004 | Chin |
| 2004/0186346 A1 | 9/2004 | Smith |
| 2004/0230100 A1 | 11/2004 | Shluzas |
| 2005/0273132 A1 | 12/2005 | Shluzas |
| 2005/0277811 A1 | 12/2005 | Richards |
| 2006/0041270 A1 | 2/2006 | Lenker |
| 2006/0122462 A1 | 6/2006 | Roth |
| 2006/0287583 A1 | 12/2006 | Mangiardi |
| 2007/0135679 A1 | 6/2007 | Hunt |
| 2007/0232874 A1 | 10/2007 | Ince |
| 2008/0100061 A1 | 5/2008 | Sage |
| 2008/0109026 A1 | 5/2008 | Kassam |
| 2008/0119693 A1 | 5/2008 | Makower |
| 2009/0048622 A1 * | 2/2009 | Wilson ............... A61B 17/3431 606/190 |
| 2009/0312611 A1 | 12/2009 | Mangiardi |
| 2010/0010315 A1 | 1/2010 | Mangiardi |
| 2012/0016316 A1 | 1/2012 | Zhuang |
| 2012/0035424 A1 | 2/2012 | Schulte |
| 2012/0071748 A1 * | 3/2012 | Mark ............. A61B 17/320016 600/411 |
| 2012/0253375 A1 | 10/2012 | Mark |
| 2012/0289816 A1 | 11/2012 | Mark |
| 2013/0066154 A1 | 3/2013 | Mangiardi |
| 2013/0102851 A1 | 4/2013 | Mark |
| 2013/0102886 A1 | 4/2013 | Mark |
| 2013/0204095 A1 | 8/2013 | Mark |
| 2013/0204287 A1 | 8/2013 | Mark |
| 2014/0107426 A1 | 4/2014 | Wilson |
| 2014/0171873 A1 | 6/2014 | Mark |
| 2014/0187922 A1 | 7/2014 | Mark |
| 2016/0015374 A1 | 1/2016 | Gifford |

FOREIGN PATENT DOCUMENTS

| | | |
|---|---|---|
| JP | 02289221 | 11/1990 |
| JP | 05344978 | 12/1993 |
| JP | 9224943 | 9/1997 |
| JP | 2000287915 | 10/2000 |
| JP | 2003153907 | 5/2003 |
| RU | 45928 | 6/2005 |
| RU | 55570 | 8/2006 |
| SU | 131027 | 3/1959 |
| SU | 349136 | 9/1972 |
| SU | 585840 | 1/1978 |
| SU | 1521465 | 11/1989 |
| WO | 0143627 | 6/2001 |
| WO | 2006050225 | 1/2006 |
| WO | 2006017507 | 2/2006 |
| WO | 2006050047 | 5/2006 |
| WO | 2013063027 | 1/2013 |
| WO | 2014137530 | 1/2014 |
| WO | 2014137551 | 1/2014 |

OTHER PUBLICATIONS

Alexander, et al. "Chapter 20: Stereotactic Frame Systems: The COMPASS System," Advanced Neurosurgical Navigation, 1999, pp. 267-277. 13 pages.

Amstutz, C., et al., "A-Mode Ultrasound-Based Registration in Computer-Aided Surgery of the Skull," Arch Otolaryngol Head Neck Surg. 2003; 129(12):1310-1316.

Andrews, R.J., et al., "A review of brain retraction and recommendations for minimizing intraoperative brain injury," Neurosurgery 1993; 33(6): 1052-1063.

Burtscher, J., et al., "Neuroendoscopy Based on Computer Assisted Adjustment of the Endoscope Holder in the Laboratory.," Minimum Invasive Neurosurgery 2003; 46:208-214.

Decision for Rejection for Patent Application No. 2009-539227 dated May 31, 2013.

Eldeib, A.M., et al., "Rigid neuroendoscope navigation system for minimally invasive surgery," Engineering in Medicine and Biology, 1999. Abstract only.

Engh, et al. NeuroendoportSM surgery facilitates removal of hard-to-reach brain tumors, University of Pittsburgh Neurosurgery News, vol. 10, No. 2, 2009. 8 pages.

Entire patent prosecution history of U.S. Appl. No. 11/155,175, filed Jun. 17, 2005, entitled, "Surgical Access Instruments for Use With Delicate Tissues."

Entire patent prosecution history of U.S. Appl. No. 11/665,667, filed Apr. 18, 2007, entitled, "Apparatus and methods for performing brain surgery."

Entire patent prosecution history of U.S. Appl. No. 12/545,686, filed Aug. 29, 2009, entitled, "Surgical Access Instruments for Use With Delicate Tissues."

Entire patent prosecution history of U.S. Appl. No. 12/545,719, filed Aug. 21, 2009, entitled, "Surgical Access Methods for Use With Delicate Tissues," now U.S. Pat. No. 8,409,083, issued Apr. 2, 2013.

Entire patent prosecution history of U.S. Appl. No. 13/431,280, filed Mar. 27, 2012, entitled, "Tissue Retractor Apparatus and Methods."

Entire patent prosecution history of U.S. Appl. No. 13/674,507, filed Nov. 12, 012, entitled, "Tissue Retractor Apparatus and Methods."

(56) References Cited

OTHER PUBLICATIONS

Entire patent prosecution history of U.S. Appl. No. 14/134,360, filed Dec. 9, 2013, entitled, "Apparatus and Methods for Performing Brain Surgery."
Extended European Search Report for EP 08 840 022.5, The Hague, Mar. 18, 2013.
Fukamachi, A., et al., "Postoperative intracerebral hemorrhages: a survey of computed tomographic findings after 1074 intracranial operations," Surgery Neurol 1985; 23(6); 575-580. Abstract only.
Greenfield, et al. "Stereotactic Minimally Invasive Tubular Retractor System for Deep Brain Lesions," Operative Neurosurgery 2, vol. 63, Oct. 2008, pp. 334-340. 7 pages.
Greenfield, JP, et al., "Stereotactic minimally invasive tubular retractor system for deep brain lesions," Neurosurgery 2008; 63(4): 334-339. Abstract only.
Gumprecht, H., et al., "Neuroendoscopy Combined with Frameless Neuronavigation," 2000, pp. 129-131, 14(2), British Journal of Neurosurgery.
Hellwig, D., et al. "Neuroendoscopic Treatment for Colloid Cysts of the Third Ventricle: The Experience of a Decade," Neurosurgery, Mar. 2003; 52(3):525-533. Abstract only.
Herrera, S. et al., "Use of Transparent Plastic Tubular Retractor in Surgery for Deep Brain Lesions: A Case Series," Surgical Technology International XIX, pp. 1-4, published in 2010.
Hilton et al., "METRx Microdiscectomy Surgical Technique," Medtronic Sofamor Danek publication, 2001, 20 pages.
International Preliminary Report on Patentability and Written Opinion for International Application No. PCT/US2006/061246 dated Jun. 3, 2009.
K043602 510(k) Summary, Feb. 23, 2005.
K060973 510(k) Summary, Jul. 26, 2006.
Kelly, et al. "The stereotaxic retractor in computer-assisted stereotaxic microsurgery," Journal of Neurosurgery, vol. 69, Aug. 1988, pp. 301-307, 7 pages.
Konen, W., et al., "An Image-Based Navigation Support System for Neuroendoscopic surgery," R. Ahlers (ed.) 5. Symposium Bilderarbeitung 1997, Technische Akademie Essingen. pp. 1-8.
Kubo, S., et al., "A Newly Designed Disposable Introducer Sheath for a Ventricular Fiberscope," Minimum Invasive Neurosurgery 2004; 47(2): 124-126. Abstract only.
Lemole, G.M., et al., "Cranial Application of Frameless Stereotaxy," Barrow Neuological Institute 2001; 17(1): 1-12.
McInerney, J., et al., "Frameless Stereotaxy of the Brain," The Mount Sinai Journal of Medicine 2000; 67(1): 300-310.
Mettler, L., et al., "Optical trocar systems: laparpscopic entry and its complications (a study of cases in Germany)," Gynaecological Endoscopy 1999; 8(6): 383-389. Abstract only.
Office Action mailed Jul. 27, 2015 for U.S. Appl. No. 13/674,507.
Office Action mailed Jul. 7, 2015 for U.S. Appl. No. 14/134,360.
Ogura, K., et al., "New microsurgical technique for intraparenchymal lesions of the brain: transcylincer approach," Aeta Neurochirurgica (Wien) 2006; 148: 779-785.
OShaughnessy, P., "New Brain tumor technology helps man who took two bullets to the head return to normal life," Daily News, Jun. 19, 2011.
Otsuku, T., et al., "Stereotactic Guiding Tube for Open-System Endoscopy: A New Approach for Stereotactic Endoscopic Resection of Intra-Axial Brain Tumors," Neurosurgery 1990; 27(2): 326-330.
Preliminary Amendment and Request for Interference for U.S. Appl. No. 14/134,360 dated Dec. 23, 2013.
Prevedello, et al. "Vycor ViewSite TC: Endoscope guided Intraparenchimal Brain Tumor Ressection," Ohio State University Medical Center Minimally Invasive Neurosurgery, 2 pages.
Rampini, P., et al., "Stereotactically guided endoscopy for the treatment of arachnoid cysts." Pediatric Neurosurgery 1998; 29(2): 102-104. Abstract only.
Raza.et al. "Minimally Invasive Trans-Portal Resection of Deep Intracranial Lesions," Minimally Invasive Neurosurgery, vol. 54, Feb. 2011, pp. 1-7.
Recinos, et al. "Use of a minimally invasive tubular retraction system for deep-seated tumors in pediatric patients," Journal of Neurosurgery: Pediatrics, vol. 7, May 2011, pp. 516-521. 6 pages.
Ross, D.A., "A simple stereotactic retractor for use with the Leksell stereotactic system," Neurosurgery 1993; 32(3): 475-476. Abstract only.
Scholz, M., et al., "Development of an Endoscopic Navigation System Based on Digital Image Processing," Computer Aided Surgery 1998; 3(3): 134-143. Abstract only.
Scholz, M. et al., "Virtual image navigation: a new method of control intraoperative bleeding in neuroendoscopic surgery," Neurosurg Focus 2000; 8(6): 1-8.
Shults, et al. "Neuro-Opthalmic Complications of Intracranial Catheters," Neurosurgery, vol. 33, No. 1, Jul. 1993, pp. 135-138. 4 pages.
Slavin et al., "Testimonials," no date but admitted as prior art between Jun. 17, 2005 and Mar. 27, 2012.
Spetzger U., et al., "Navigational microneurosurgery: experience with Easy Guide Neuro," Medicamundi 1997; 41(1): 28-35.
UPMC: Minimally Invasive Brain Surgery. Legacy of Innovations. Breakthroughs in minimally invasive brain surgery at UPMC. 2014.
Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012.
Zhong, J., et al., "Brain retraction injury," Neurological Research 2003; 25: 831-838.
"Neuronavigation" from Wikipedia dated Jul. 30, 2014.
International Search Report and Written Opinion for International Application No. PCT/US2015/030528 mailed Aug. 14, 2015.
Wang, W.H. et al., "Endoscopic hematoma evacuation in patients with spontaneous supratentorial intracerebral hemorrhage," Journal of the Chinese Medical Associations, vol. 78, 2015, pp. 101-107.
Tao, X. et al., "Microsurgical resection for lateral ventrical meningiomas with neuronavigation and tubular retractor system," Chin. J. Neurosurg, vol. 31, No. 4, 2015, pp. 332-336 (abstract only).
Rymarczuk, G.N. et al., "Use of a Minimally Invasive Retractor System for Retrieval of Intracranial Fragments in Wartime Trauma," World Neurosurgery, 2015, pp. 1-26.
Shoakazemi, A. et al., "A 3D endoscopic transtublar transcallosal approach to the third ventricle," J. Neurosurg, 2015, pp. 1-10.
Nagatani, K. et al., "High-Definition Exoscope System for Microneurosurgery: Use of an Exoscope in Combination with Tubular Retraction and Frameless Neuronavigation for Microsurgical Resection of Deep Brain Lesions," No Shinkei Geka, Jul. 2015, vol. 43, No. 7, pp. 611-617 (Abstract Only).
Nico Corporation Press Release, "NICO Corporation Gains Market Expansion after Multiple Published Clinical Articles Support Access Technology for Deep Brain Lesions," May 5, 2015, pp. 1-2.
Ding, D. et al., "Endoport-assisted microsurgical resection of cerebral cavernous malformations," J. Clin. Neurosci., Jun. 2015, vol. 22, No. 6, pp. 1025-1029 (Abstract Only).
Del Ray Medical Center Press Release, "Advanced Neuroscience Network Brings New Innovations in Neurosurgery to South Florida," May 13, 2015, pp. 1-6.
Final Office Action for U.S. Appl. No. 14/134,360, dated Jan. 12, 2016.
Notice of Allowance mailed Mar. 11, 2016 for U.S. Appl. No. 14/134,360.
International Preliminary Report on Patentability for International Application No. PCT/US2015/030528, dated Nov. 15, 2016, 7 pages.
Final Office Action for U.S. Appl. No. 14/727,374, mailed Nov. 23, 2016, 14 pages.
Non Final Office Action for U.S. Appl. No. 14/711,305, mailed Dec. 7, 2016, 42 pages.
Notice of Allownce for U.S. Appl. No. 14/727,374, mailed Jan. 19, 2017, 9 pages.
Notice of Allowance for U.S. Appl. No. 14/711,305, mailed Apr. 18, 2017, 11 pages.
Extended European Search Report for European Application Application No. 15793215.3, dated Mar. 24, 2017, 6 pages.
Non Final Office Action for U.S. Appl. No. 14/727,361, mailed Jul. 14, 2016, 31 pages.

(56) References Cited

OTHER PUBLICATIONS

Non Final Office Action for U.S. Appl. No. 14/427,374, mailed Jul. 22, 2016, 35 pages.
Notice of Allowance for U.S. Appl. No. 14/727,361, mailed Sep. 21, 2016, 8 pages.

* cited by examiner

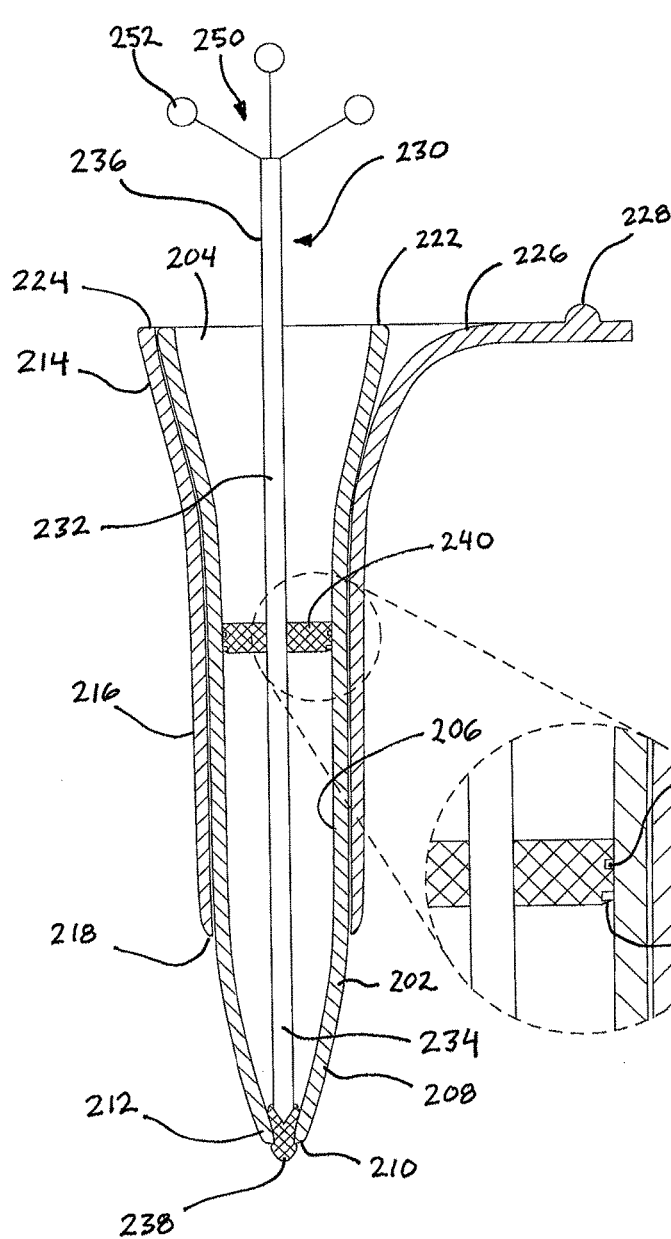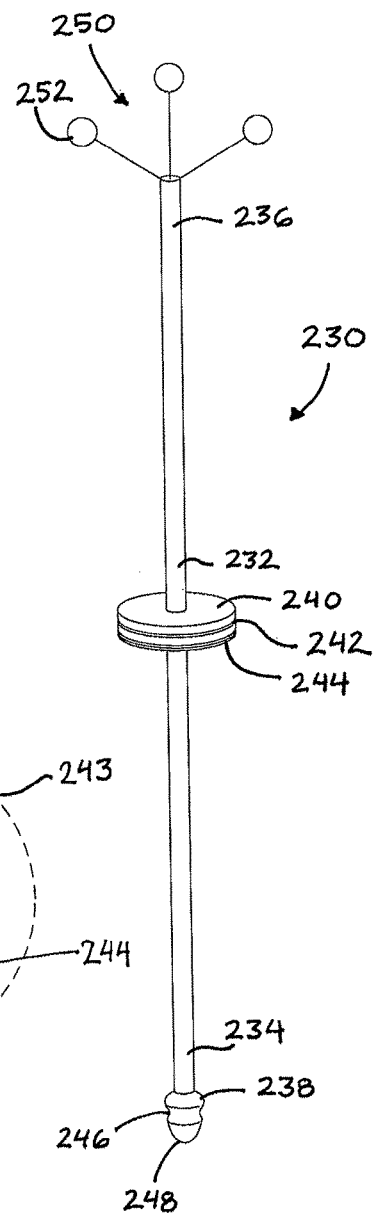

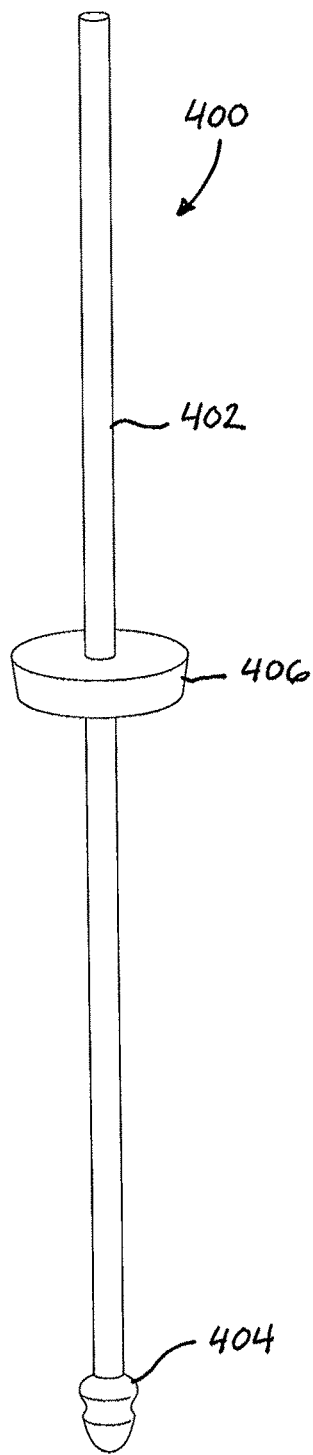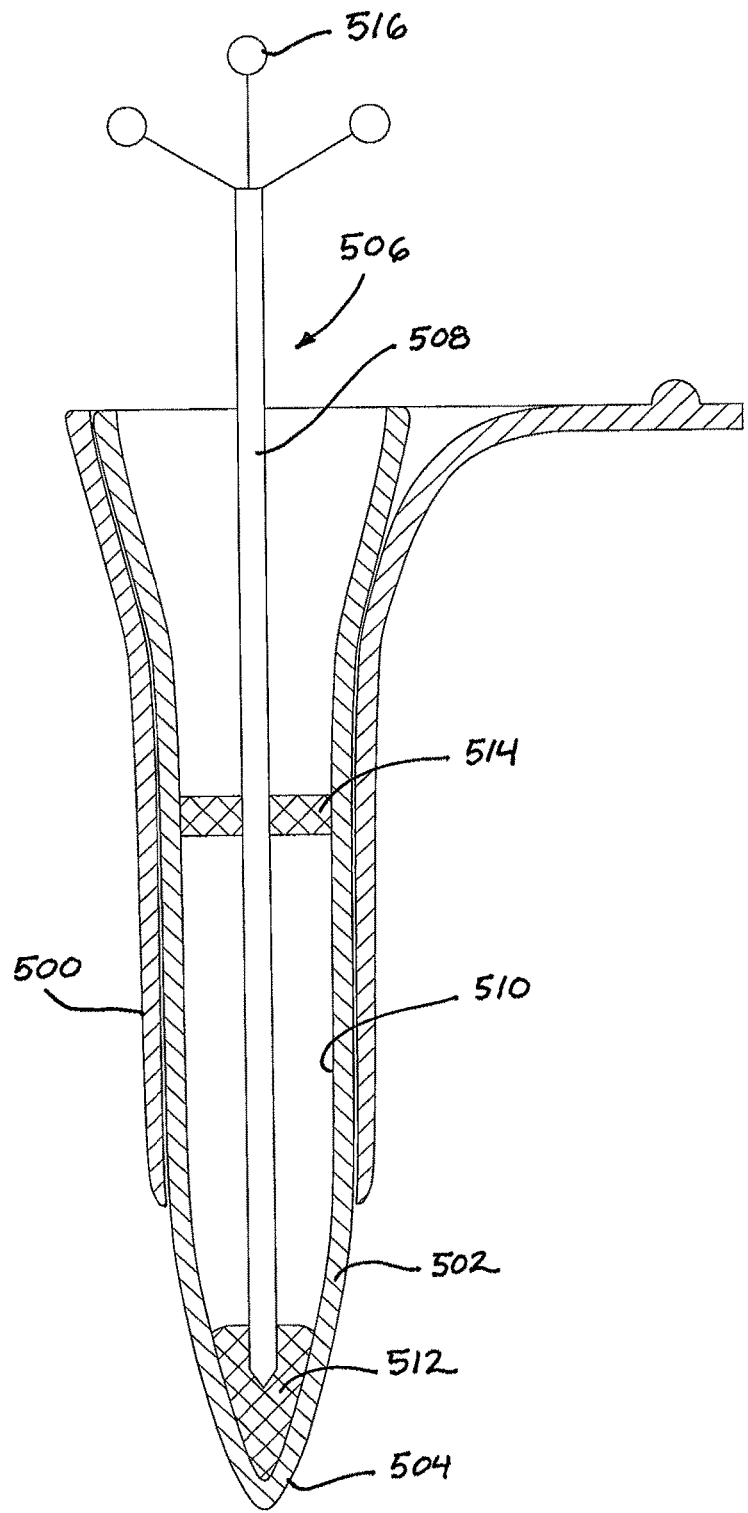

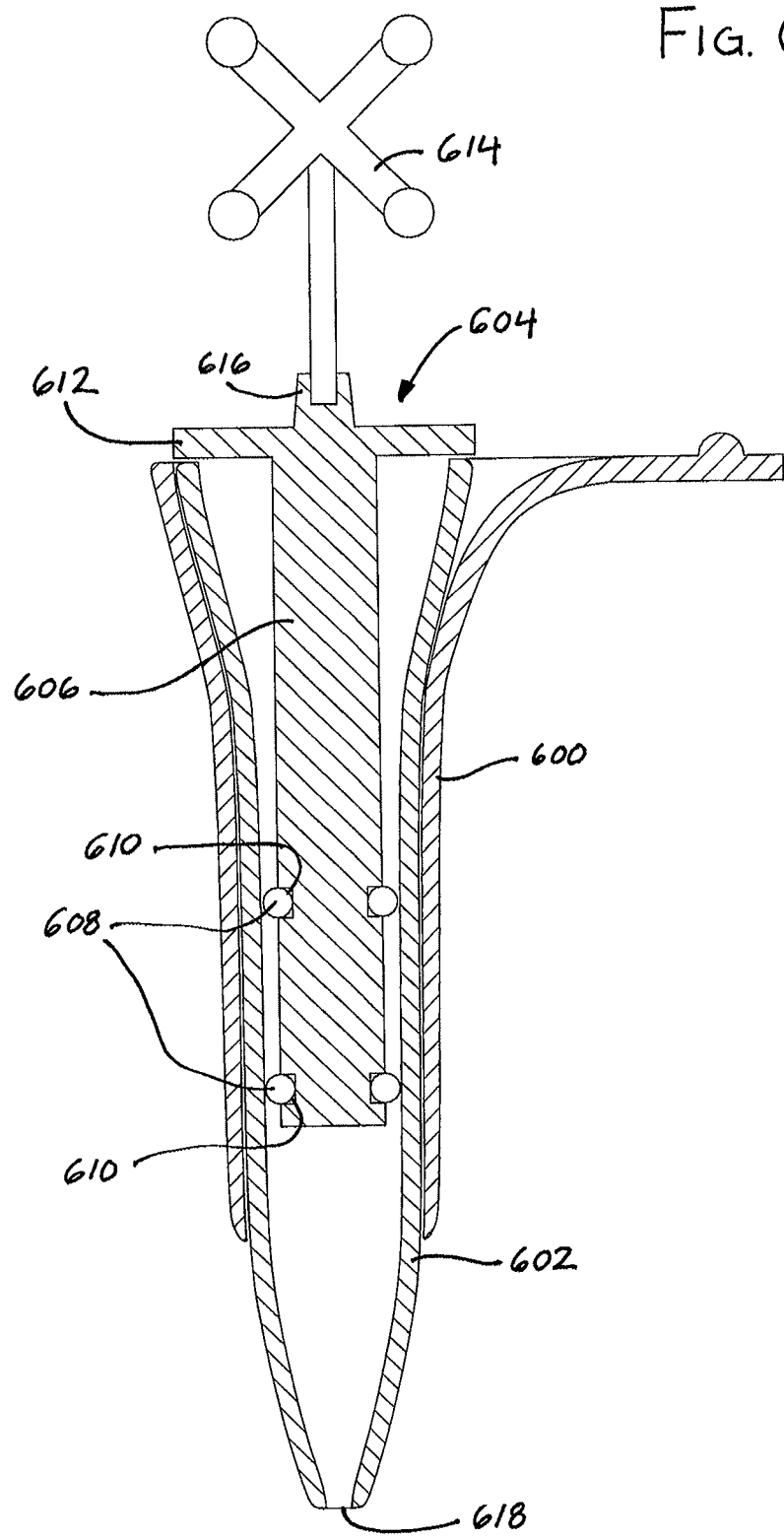

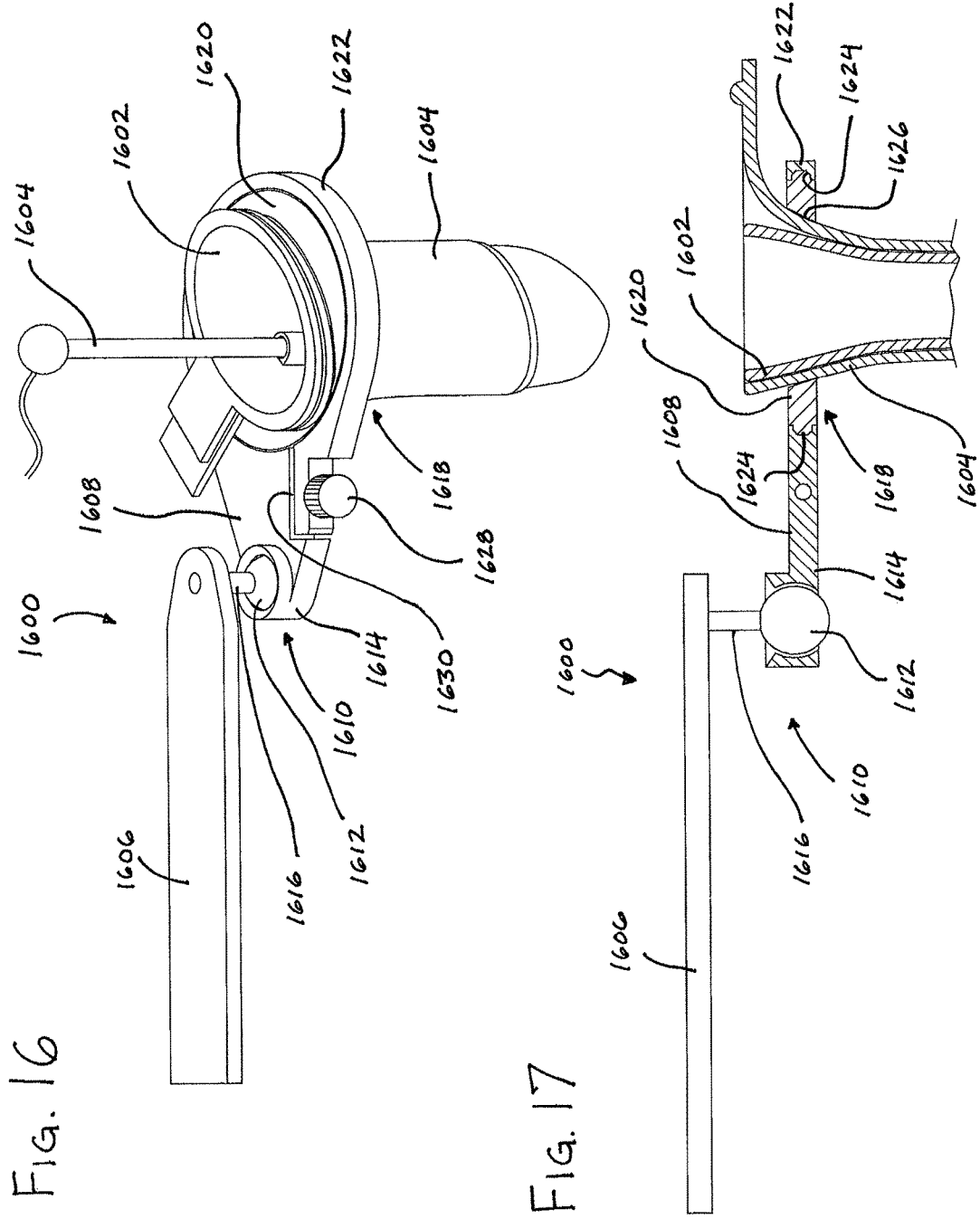

TISSUE RETRACTOR APPARATUS AND METHODS

CROSS REFERENCE TO RELATED APPLICATIONS

This application is a continuation of Ser. No. 13/674,507 filed Nov. 12, 2012, which is a continuation of U.S. application Ser. No. 13/431,280, filed Mar. 27, 2012, which is a continuation-in-part of Ser. No. 12/545,686, filed Aug. 21, 2009, which is a continuation of Ser. No. 11/155,175, filed Jun. 17, 2005, the entire contents of which are incorporated herein by reference.

FIELD OF THE INVENTION

The present invention relates to surgical retractor systems, such as brain retractors, and more specifically to devices that may be used to enhance the functionality of such retractors.

BACKGROUND OF THE INVENTION

A variety of different devices have been used to retract delicate tissue during surgical procedures. One such device is illustrated in United States Patent Publication Number 2010/0010315 ("Mangiardi"), to which this application claims priority and which is incorporated herein by reference in its entirety. Mangiardi shows two general versions of a retractor for delicate tissue. One version is a closed-channel retractor in the form of a tube (see, e.g., Mangiardi FIG. 3), and the other is an open-channel retractor in the form of a curved channel (see, e.g., Mangiardi FIG. 23).

FIG. 1 of this application illustrates a soft tissue retractor system such as found in Mangiardi. The retractor system includes a hollow retractor 100, and an introducer 102 that is selectively inserted into the retractor 100. The retractor 100 and/or introducer 102 may include a handle 104 to facilitate manipulation and placement of the retractor system, and a lock to hold the introducer and retractor together. The illustrated handle 104 is molded integrally with the retractor 100, but it may be a separate part. The handle 104 may be configured to connect to a clamp 106, such as the standard surgical clamp 106 shown in FIG. 1. In this example, the handle 104 has a ridge 108 that fits into a corresponding groove 110 on the clamp 106, to prevent relative rotation between the two when engaged. Modifications to this design are described in Mangiardi.

A retractor system such as shown in FIG. 1 is often used by inserting the introducer 102 into the retractor 100 and locking it in place, so the two can be moved and manipulated as a unit. The combined introducer/retractor system is inserted into the patient's body and moved to the surgery site, and then the introducer 102 is unlocked and removed to permit access to the site through the retractor 100. When the unit is in place (either before or after the introducer 102 is removed), the handle 104 may be locked to a clamp 106 to hold the retractor 100 in place. An example of this procedure is shown in FIGS. 16-20 of Mangiardi. Surgeons using the Mangiardi retractor sometimes do not use a clamp to hold the retractor at the surgery site, and often manually manipulate the retractor to access different parts of the surgery site during the surgical procedure. The introducer/retractor system and the retractor may be manipulated by holding the proximal ends of the introducer or retractor or by holding the handle.

The device shown in Mangiardi may have a transparent introducer 102 and/or retractor 100, and surgeons using such devices advantageously use the transparent introducer and retractor to manually guide the unit to the surgery site. While it has been found that visual guidance by looking through the introducer 102 is very beneficial, it also has been found that some form of additional guidance or navigation may be desired in some cases. For example, in some cases, surgeons have used a stylet (a narrow elongated rod) to guide the movement of the introducer/retractor system. In such cases, the stylet is advanced to the surgery site, and then the interlocked introducer/retractor system is slid over the stylet until it reaches the surgery site. This is facilitated by the inclusion of a hole at the tip of the introducer that fits around the stylet. If the hole through the tip of the introducer is absent, this method cannot be used.

It has been found that some surgeons using the above procedure may use a stylet that is integrated into a computer navigation system. For example, the stylet may include a so-called "starburst" or the like, on the stylet's proximal end (i.e., the end opposite the distal end that is inserted to the surgical site). This and other navigation systems are known in the art. For example, frameless navigation systems and other computerized guidance systems and methods are described in U.S. Publication No. 2001/0027271, and others, and are commercially available from companies such as Medtronic, Inc., Stryker, BrainLab, AG, Ge Healthcare. The foregoing reference is incorporated herein by reference in its entirety. As used herein, "computerized guidance" encompasses any method of guiding a device to or at a surgical site that relies on computer visualization and/or control, as opposed to direct visual inspection and/or manual movement. Mangiardi briefly notes the possibility of using stereotactic guidance or navigation in conjunction with a surgical retractor, but does not illustrate or describe this procedure or any apparatus for accomplishing this objective.

While computerized surgical guidance systems are well-known, a number of limitations exist with respect to their use with introducer/retractor systems, and particularly with systems like those shown in Mangiardi. For example, while some surgeons use computerized guidance to direct a stylet to the surgery site, and then slide the introducer/retractor system over the stylet to the site, the movement of the introducer/retractor may be somewhat imprecise and the process can be unduly cumbersome. This method also is not available if the introducer/retractor system does not have a through-hole that fits over the stylet (due either to the absence of a hole or a hole that is too small). In addition, the stylet does not provide a view of the tissue through which it is advanced, so there is no visual means to perceive and avoid critical tissue (e.g., major blood vessels or nerves) when inserting a stylet before inserting a retractor/introducer system. Also, the small-diameter stylet may sever delicate tissue cells, such as grey or white brain matter, rather than moving the cells aside and passing between them as would be expected to happen when advancing the introducer/retractor system.

While preexisting navigation system devices have been used with delicate tissue introducers and retractors, there still exists a need to provide alternative solutions. In addition, there is a need to provide alternatives to existing systems for manipulating, introducing and holding retractors.

SUMMARY

In one exemplary embodiment, there is provided a delicate tissue retraction system having a hollow tubular retractor, a hollow tubular introducer, and a navigation module.

The retractor has a proximal retractor end and a distal retractor end. The introducer has a proximal introducer end, a distal introducer end, and an inner passage extending from the distal introducer end to the proximal introducer end, the inner passage being defined by a passage wall having a width dimension that increases in size from the distal introducer end to the proximal introducer end. The introducer is configured to be removably installed within the retractor with the proximal introducer end being adjacent the proximal retractor end and the distal introducer end extending beyond the distal retractor end. The navigation module includes a shaft having a proximal shaft end, a distal shaft end, a middle shaft portion between the proximal shaft end and the distal shaft end, and a navigation unit mounted to the proximal shaft end. The navigation module is removably installable within the introducer with the distal shaft end contained generally within the introducer, the middle shaft portion spaced from the passage wall, and the navigation module outside the introducer. The navigation module indicates the location of one or more points on at least one of the retractor and the introducer to a navigation system.

The recitation of this summary of the invention is not intended to limit the claims of this or any related or unrelated application. Other aspects, embodiments, modifications to and features of the claimed invention will be apparent to persons of ordinary skill in view of the disclosures herein.

BRIEF DESCRIPTION OF THE DRAWINGS

The following Figures are provided to help explain exemplary embodiments of the invention, but are not intended to limit the claimed invention in any way.

FIG. 2 is a cutaway side elevation view of an exemplary retractor system navigation module and retractor/introducer system.

FIG. 3 is an isometric view of the exemplary retractor system navigation module of FIG. 2.

FIG. 4 is an exemplary embodiment of a tip closure member that may be used with embodiments of introducers having top openings.

FIG. 5 is a cutaway side elevation view of another exemplary retractor system navigation module and retractor/introducer system.

FIG. 6 is a cutaway side elevation view of another exemplary retractor system navigation module and retractor/introducer system.

FIG. 16 is an isometric view of another embodiment of an introducer/retractor system manipulation arm.

FIG. 17 is a partial cutaway side view of the embodiment of FIG. 16.

DETAILED DESCRIPTION OF PREFERRED EMBODIMENTS

Figure 1:
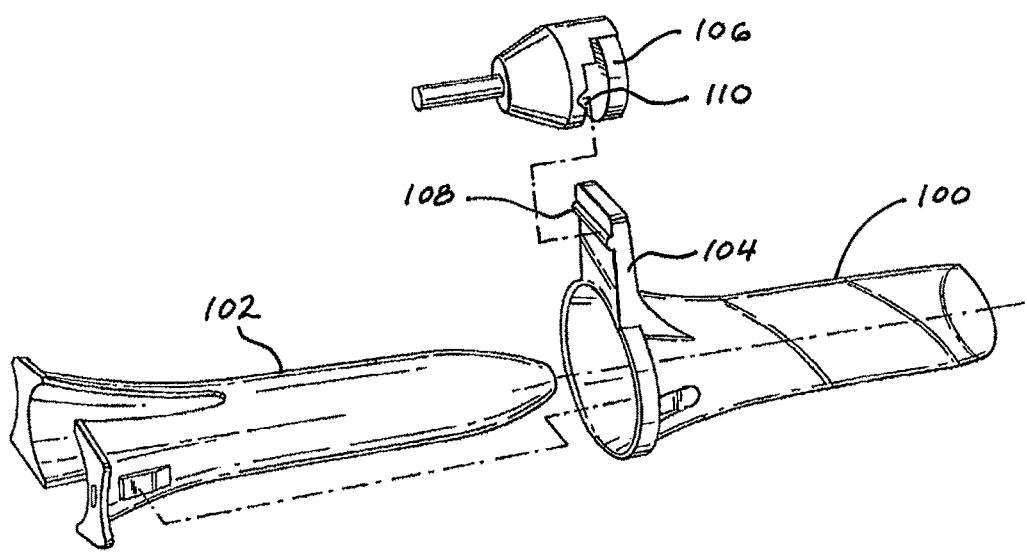
FIG. 1 is an example of a delicate tissue retractor system that may be used with embodiments of the present invention.

The present disclosure provides exemplary embodiments of various apparatus that can be used with known or future tissue retractor systems. Such features include, for example, guidance systems for monitoring and/or controlling the movement of the retractor system and a clamp that can be used to manipulate the system. The features described herein may be used together or separately, and may be modified as appropriate or desired for the particular application. For illustration, the exemplary embodiments are described herein as they may be adapted for use with a soft tissue retractor such as the one shown in FIG. 1. It will be apparent to persons of ordinary skill in the art, however, that other modifications may be made to embodiments used with devices like the exemplary retractor in FIG. 1, and that other versions may be constructed for use with other devices that are not similar to this exemplary embodiment devices.

FIGS. 2 and 3 illustrate a first embodiment of a navigation system that may be used with a combined introducer/retractor system. In this embodiment, the introducer/retractor system comprises a hollow retractor 200 into which a hollow introducer 202 is releasably installed. The introducer 202 and retractor 200 may comprise structures as described in Mangiardi, or have other shapes or configurations. In this example, the introducer 202 has a tapered proximal end 204, an approximately straight or slightly tapered center portion 206, and a tapered distal end 208 that extends beyond the retractor 200 and terminates at a tip 210. The tip 210 of the introducer 202 has a tip opening 212 that passes through it. The retractor 200 has a tapered proximal end 214 and a straight or slightly tapered center portion 216, and terminates at the end of the center portion 216 at an opening 218. The outer wall of the retractor 200 may be chamfered or rounded around the perimeter of the opening 218 to help prevent local concentration of pressure when the introducer 202 is removed. The retractor 200 and introducer 202 may be a tube (i.e., a closed channel) having any suitable profile (i.e., shape as viewed along their longitudinal axis 220) that is circular, semicircular, rectilinear, oval, elliptical, or flattened (i.e., provided with one long dimension and one short dimension) to help prevent unnecessary displacement of and pressure on tissue during insertion and use. The retractor 200 and/or introducer 202 also may have an open channel shape (i.e., non-tubular) having a semicircular profile or other profile. For example, the introducer 202 may be tubular with a closed half-circular profile (such as a "D" shape), and the retractor 200 may be an open channel with an open half-circular profile (e.g., a "C" shape) that nests over the introducer profile. The dimensions and shapes of the foregoing features be varied to address different surgical needs. Exemplary dimensions and shapes are provided in the Mangiardi reference. Such devices may be sold in kits that have introducers and retractors of various shapes and/or sizes to provide the surgeon with sufficient variety to address a number of situations.

The introducer 202 and/or retractor 200 may have transparent walls through which the surgeon can see underlying tissue. For example, the walls may be made of glass, polycarbonate or other transparent or semi-transparent materials. While transparent walls are preferred, it is not required in all embodiments, such as embodiments in which a navigation system supplants the surgeon's reliance on vision to position the introducer 202 and retractor 200. The proximal surfaces of the retractor 200 and introducer (222 and 224, respectively) may be treated to render them non-reflective or glare-resistant, such as by painting them matte black or overmolding a matte layer of material. The walls of the introducer 202 and/or retractor 200 may also be used as a light guide to transmit light to the surgical site at the distal end of the retractor 200, as known in the art and shown, for example, in U.S. Pat. No. 3,417,746, which is incorporated by reference herein.

The retractor 200 may include a handle 226 that is shaped and sized to be retained in a clamp and/or to help a surgeon to manipulate the retractor 200. In this embodiment, the handle 226 includes a raised bead 228 that fits into a corresponding groove on a clamp to provide a firmer connection between the handle and the clamp. Of course, other retention features may be provided in other embodiments (e.g., the bead may be formed on the clamp, and a corresponding groove formed on the handle 226).

A navigation module 230 is selectively installed within the introducer 202. In this example, the navigation module 230 may comprise a standard navigation stylus having a shaft 232 and a navigation unit 250 at the proximal end 236 of the shaft 232. A computer navigation system tracks the movement of the navigation unit 250 to calculate of the location of the distal end 234 of the shaft 232, as known in the art. When installed in the introducer/retractor system, the shaft 232 extends generally along the longitudinal axis 220 from the distal shaft end 234 to the proximal shaft end 236. In this embodiment, the distal shaft end 234 preferably is located at or near the distal end 208 of the introducer 202. Also in this embodiment, the proximal shaft end 236 is located outside and spaced from the proximal introducer surface 222. It is envisioned that these locations may be modified without departing from the general spirit of this disclosure. For example, the proximal shaft end 236 may be located at or even somewhat within the proximal introducer end 204, provided whatever navigation system is associated with the navigation module 230 is still able to operate effectively (e.g., by programming it to associate the displaced tip of the stylus shaft with the actual location of the distal end of the introducer). Infrared or other visual devices might require some part of the navigation module 230 to be located outside the proximal end 204 of the introducer 202, but wired electronic systems or navigation units that do not rely on visual contact with a navigation system might be mounted well within the confines of the introducer 202. While the distal shaft end 234 may, in some embodiments, protrude beyond the distal end 208 of the introducer, it is anticipated that locating the distal shaft end 234 at or short of the distal end of the introducer 208 may provide a particular benefit by reducing the likelihood that the distal shaft end 234 will interfere with tissue as the system is being advanced through the tissue. In this configuration (such as shown in FIG. 2), the navigation module 230 does not interfere with the benefit of gentle tissue separation that is provided by the introducer/retractor system.

The navigation module 230 may be secured to or located within the introducer 202 by any suitable means. In the embodiment of FIG. 2, the navigation module 230 is secured by one or more plugs that resiliently engage the introducer 202. For example, in the shown embodiment, a tip plug 238 is provided at the distal shaft end 234 and a shaft plug 240 is provided along the shaft 232. The plugs 238, 240 preferably hold the navigation module in a generally fixed position relative to the introducer, so that the navigation unit 230 and the introducer/retractor system move together as a unit during insertion to the surgery site. It will be appreciated that any movement between the navigation module 230 and the introducer 202 may cause some inaccuracy in computer navigation, but some minor relative movement may be within operating tolerances.

The plugs 238, 240 preferably are made of a resilient, tactile material to secure the navigation module 230 to the introducer 202 by frictional engagement. The plugs 238, 240 may be attached to the shaft 232 either permanently (such as by overmolding) or removably (such as by friction fitment). One material that is expected to be suitable for the plugs is silicone rubber, but other materials may be used. Using such resilient material, the navigation module 230 can be inserted into the introducer 202 and pressed in place with a force to slightly compress the plugs 238, 240. The compressed plugs 238, 240 are expected to exert a restoring force against the inner walls of the introducer 202, which will hold the navigation module 230 in place until it is removed by pulling it towards the proximal introducer end 204. By connecting the navigation module 230 to the introducer 202 when the parts are dry, the engagement force can be maximized. However, it is expected that materials such as silicon rubber for the plugs 238, 240 and polycarbonate for the inner wall of the introducer 202 will maintain good engagement even in the presence of fluids present during typical surgical procedures, and possibly even if the materials are wet when connected. In order to minimize the likelihood that fluid will interfere with the connection, features may be provided to address issues that may be associated with the presence of fluids. For example, one or more grooves may be provided in the plugs to trap and retain moisture, and the plugs may have one or more integral wiping features 244 (e.g., flexible circumferential protrusions) to displace fluid that might be present during engagement.

The tip plug 238 and shaft plug 240 may be shaped to conform generally to the inner walls of the introducer 202. For example, the plugs 238, 240 may have an ovate profile if the introducer 202 is ovate, or a round profile is the introducer 202 is round. The plugs 238, 240 may be tapered or otherwise shaped to correspond to the longitudinal shape of the inner wall of the introducer 202. In the embodiment of FIGS. 2 and 3, the tip plug 238 includes a circumferential groove 246 that resiliency engages inside the introducer tip opening 212. Such a tip plug 238 may be shaped and sized to seal the tip opening 212 closed against the ingress of fluid. The distal end of the tip plug 238 may protrude beyond the end of the tip opening 212, and in that case may be shaped as a tapered or rounded cone 248 to form a smooth contour to displace tissue as the retractor/introducer unit is advanced to the surgical site. However, it is not necessary for the tip plug 238 to extend through the tip opening 212 in all embodiments. Indeed, the tip plug 238 may be spaced from the tip opening 212 and from the distal end of the introducer 202. In still other embodiments, the tip plug 238 may be omitted, and the end of the shaft 232 may be sized to rest against the inside wall of the introducer 202 at or around the tip opening 212 (if one is present) or the distal end 208 of the introducer 202.

In the embodiment of FIGS. 2 and 3, one or both plugs 238, 240 may be slidable along the shaft 232 to position the plugs 238, 240 to fit inside introducers 202 having different lengths. For example, in the shown embodiment, the shaft plug 240 is shaped as a simple ovate ring that can be slid in the longitudinal direction 220 along the shaft 232 to any desired position. Frictional engagement between the shaft plug 240 and the shaft 232 holds the shaft plug 240 in the desired position. If desired, other securements between the shaft plug 240 and the shaft 232 may be used, such as radial clamps or the like.

While the foregoing embodiment has been described using resilient plugs 238, 240, it will be appreciated that the plugs may be replaced by non-resilient members, such as solid plastic pieces that are attached to or integrally formed with shaft 232. In such an embodiment, the plugs 238, 240 may be used simply to center the navigation module 230 within the introducer/retractor system, with a retaining force being provided by the surgeon or other mechanisms. Alternatively, one or both plugs 238, 240 may engage portions of the introducer or retractor to hold them together. For example, one plug 238 may comprise an exterior thread or bayonet fitting that engages a corresponding thread or bayonet fitting formed on the inner wall of the introducer 202. These and other variations will be apparent to persons of ordinary skill in the art in view of the present disclosure.

The navigation unit 250 may be attached to the shaft 232, such as by being attached at the proximal shaft end 236. The navigation unit 250 may comprise any suitable electronic, visual or stereotactic navigation device. Examples of such devices include arrangements of LEDs (light emitting diodes) or "starbursts" comprising multiple optical reflectors, which are used to convey the physical location and orientation of the navigation unit 250 to an optical detection system set up in the operation room. Such devices may use visible-light or non-visible radiation (e.g., infrared light) to detect and track the navigation unit 250, as known in the art. Such devices are available from commercial sources, such as Medtronic, Inc., Stryker, BrainLab, AG, Ge Healthcare, and others, and need not be described in detail here. Alternatively, the navigation unit 250 may be integrally formed with the shaft 232, as known in the art. Regardless of what kind of navigation unit 250 is used, it may be necessary to program the tracking system with the dimensions of the combined introducer, retractor and navigation unit so that the program can equate the location of the navigation unit 250 to the distal end (and perhaps other dimensions) of the introducer 202. Using such programming, the tracking system can know precisely where the tip 210 of the introducer 202 is at all times.

Referring to FIG. 4, it is expected that an embodiment of a device as shown in FIGS. 2 and 3 may be useful even if no navigation unit is provided. This embodiment is a simple tip closure member 400 having a shaft 402 or other structure to which a tip plug 404 is connected. The shaft 402 fits within an introducer, such as the introducer 202 shown in FIG. 2, and the tip plug 404 engages and seals the introducer tip opening 212. The shaft 402 preferably is long enough to be accessible for removal during surgery, but this is not required. The shaft 402 may include a second plug 406, such as the tapered plug 406 shown in FIG. 4, to help hold the closure member 400 in place, but this is not strictly necessary. A second plug 406 may be desirable if it is expected that lateral movement of the shaft 402 within the introducer might accidentally dislodge the tip plug 404, however such movement may actually be desirable to help the surgeon intentionally remove the tip plug 404 when desired.

A device such as the embodiment of FIG. 4 may be useful for surgeons that prefer not to have a tip opening 212 formed in the introducer 202. That preference may be due to the expected inflow of fluids into the tip opening 212 during insertion of the introducer/retractor system to the surgery site, or for other reasons. Regardless of the reason, the tip closure member 400 is expected to provide an economical way to close and seal an introducer tip opening 212 in introducers that have such an opening.

Referring now to FIG. 5, another embodiment of a navigation module is illustrated and described. This embodiment is used with a retractor 500 and introducer 502 similar to the previously-described embodiment. In this embodiment, however, the introducer 502 does not include a tip opening, and instead has a closed tip 504. The tip 504 may be formed, for example, as a rounded, tapered cone. Here, the navigation module 506 comprises a shaft 508 that is secured to the inner wall 510 of the introducer 502 by one or more plugs 512, 514, and a navigation unit 516 such as described above. The plugs 512, 514 may be constructed as described previously, or have different constructions. For example, the tip plug 512 may be shaped as a generally conical structure instead of being adapted to fit into and seal an introducer tip opening.

It is also envisioned that a navigation module may be provided that fits introducer that have tip openings (such as shown in FIG. 2), or introducers that do not have a tip opening (such as shown in FIG. 5). For example, the tip plug 238 on the navigation module 230 of FIG. 3 may be shaped to engage the introducer regardless of whether the introducer has a tip opening or not.

Turning to FIG. 6, another embodiment of a navigation module is illustrated and described. This embodiment mounts to an interconnected retractor 600 and introducer 602 by installing within the bore of the introducer 602. In this embodiment, the navigation module 604 comprises a shaft 606 that engages the introducer, and a navigation unit 614 that is selectively connectable to the shaft 606. For example, the navigation unit 614 may be selectively mounted in a receptacle 616 at the top of the shaft 606. This makes the navigation module 604 a modular system in which different navigation units 614 may be selectively fitted to different shafts 606 to suit the particular circumstances. For example, a family of different shafts 606 may be provided, each fitting one or more introducers having different diameters, lengths, profiles or other dimensions. The receptacle 616 may be a locking cuff, a threaded opening, bayonet fittings, or any other suitable arrangement of engaging parts.

The shaft 606 may be secured to the introducer 602 by one or more resilient seals 608. The seals 608 may comprise plugs as described before, or other structures. For example, the seals 608 may comprise O-rings or other resilient members that can frictionally engage the introducer 602. O-rings may be mounted to the shaft by forming a circumferential groove 610 to retain each O-ring. The proximal end 612 of the shaft 606 may be flared outward to rest against the end of the introducer 602, to thereby provide a visual indication when the shaft 606 is fully-seated and prevent over-insertion.

In this embodiment the introducer 602 has a tip opening 618, but this is not required in all embodiments. If a tip opening is provided, it may be desirable to provide some means to seal the opening, such as a seal that extends down from the shaft 606. Alternatively, it may be desirable to permit fluid to enter the opening, and to provide some means to facilitate suction removal of that fluid. For example, a bore may be provided through the shaft 606 to permit access by a suction tube. Some means for providing suction may also be provided in the previously-described embodiments. For example, the embodiment of FIGS. 2 and 3 may include a notch formed on the upper plug 240 through which a suction tube or other devices can be passed to detect the presence of and remove fluid.

The foregoing embodiments are illustrated with the navigation module being centered along the longitudinal axis of the introducer. This arrangement may be desirable to simplify the spatial relationship between the navigation unit and the end of the introducer, and give the surgeon a better sense about where the tip of the introducer is located during the surgical procedure. However, this arrangement is not necessary in all embodiments.

Figure 8:
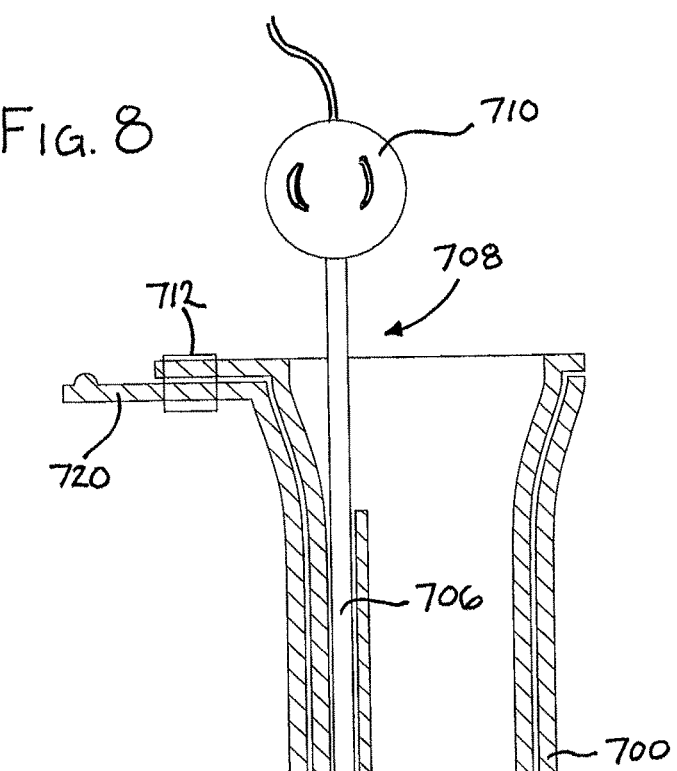
FIG. 8 is a cutaway side elevation view of the apparatus of FIG. 7.
Figure 7:
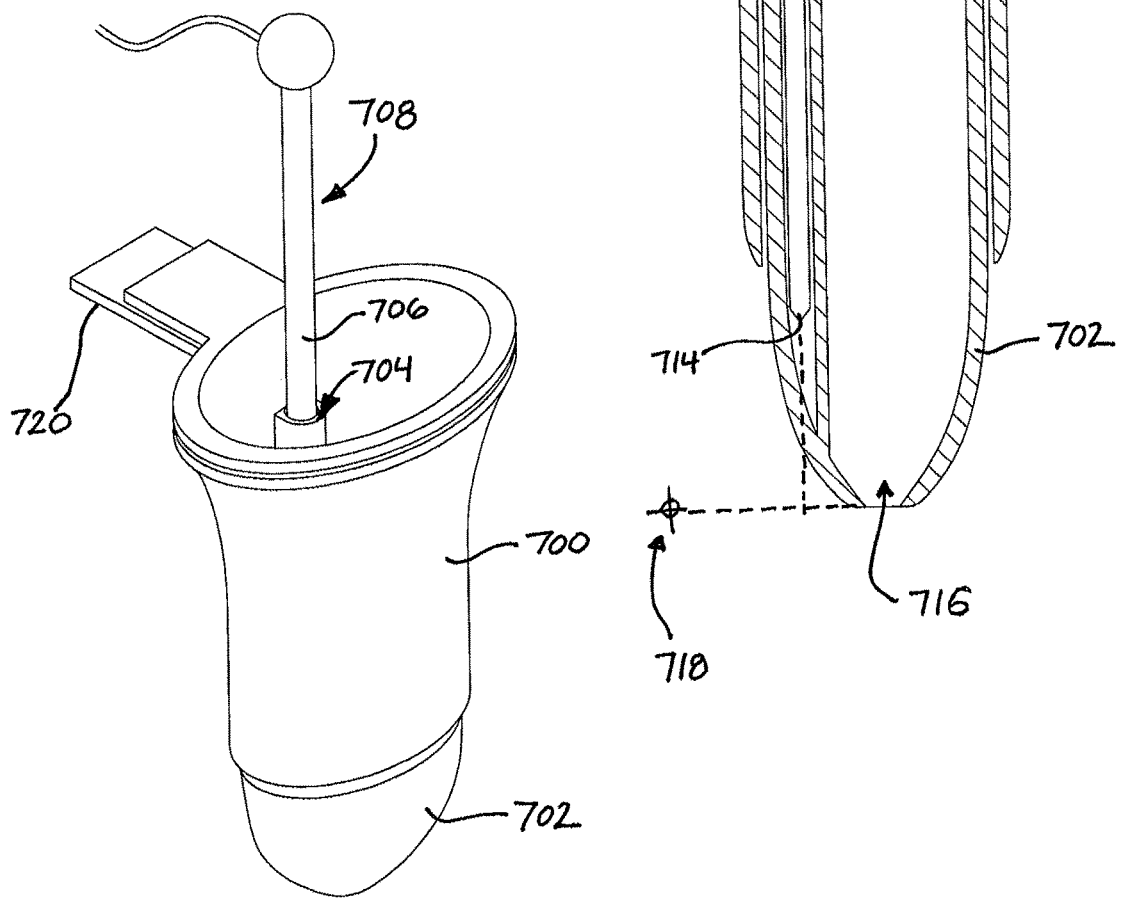
FIG. 7 is an isometric view of still another exemplary retractor system navigation module and retractor/introducer system.

FIGS. 7 and 8 illustrate an embodiment of an offset mount for a navigation module. This embodiment is also shown in relation to a nested retractor 700 and introducer 702 that are held together with a lock 712. The introducer 702 includes an internal passage 704 that is sized to receive a shaft 705 of a navigation module 708. As with the other embodiments, the navigation module 708 includes a navigation unit 710, this time shown as wired unit. The internal passage 704 may be formed integrally with the introducer using a conventional molding process, but it may alternatively be made separately and attached to the introducer. The internal passage 704 may be closed at the distal end, as shown, or it may be open to facilitate the evacuation of fluid or materials therefrom.

In the embodiment of FIGS. 7 and 8, the shaft 706 of the navigation module 708 may be somewhat loosely retained in the passage 704 by forming them with close tolerances, but not so close that there is substantial friction upon insertion or removal. In this case, the navigation module 708 may be held in place manually by the user, by gravity, or simply by contact between the parts. When the most accurate computer navigation is desired, it may be recommended to the user to apply a slight retaining force to hold the navigation module 708 snugly in place in the passage 704. Alternatively, the navigation module may be frictionally retained or locked in place by any suitable arrangement of devices. For example, plugs, threads, bayonet fittings, or seals may be provided to hold the navigation module 708 in place.

One beneficial feature of this embodiment is that the navigation module 708 is offset from the centerline of the introducer 702, and therefore interferes to a lesser degree (if at all) with the surgeon's view into the introducer. This feature makes embodiments such as this one suitable for simultaneous computer (e.g., stereotactic) and manual navigation, thus providing the benefits of both forms of navigation.

Embodiments such as this also may permit access by one or more surgical instruments without having to remove the navigation module. This may be particularly advantageous where a surgeon desires to suction fluid, or to cauterize, cut or remove tissue, during the insertion process or at any other time before the introducer is removed from the retractor. Of course, as with other embodiments described herein, the navigation module may be removed at any time to permit operations through the introducer (or to further enhance the user's view), and then replaced if desired.

It will be appreciated that the passage 704 that holds the navigation module 708 may be moved to other locations and formed in any suitable way. For example, the passage 704 may be moved to the side of the introducer 702 that is opposite the handle 720 on the retractor 700, or at other locations around the introducer 702. The passage 704 also may be formed in the wall of the retractor 700 instead of the introducer 702. These and other variations will be apparent to persons of ordinary skill in the art in view of the present disclosure.

Figure 9:
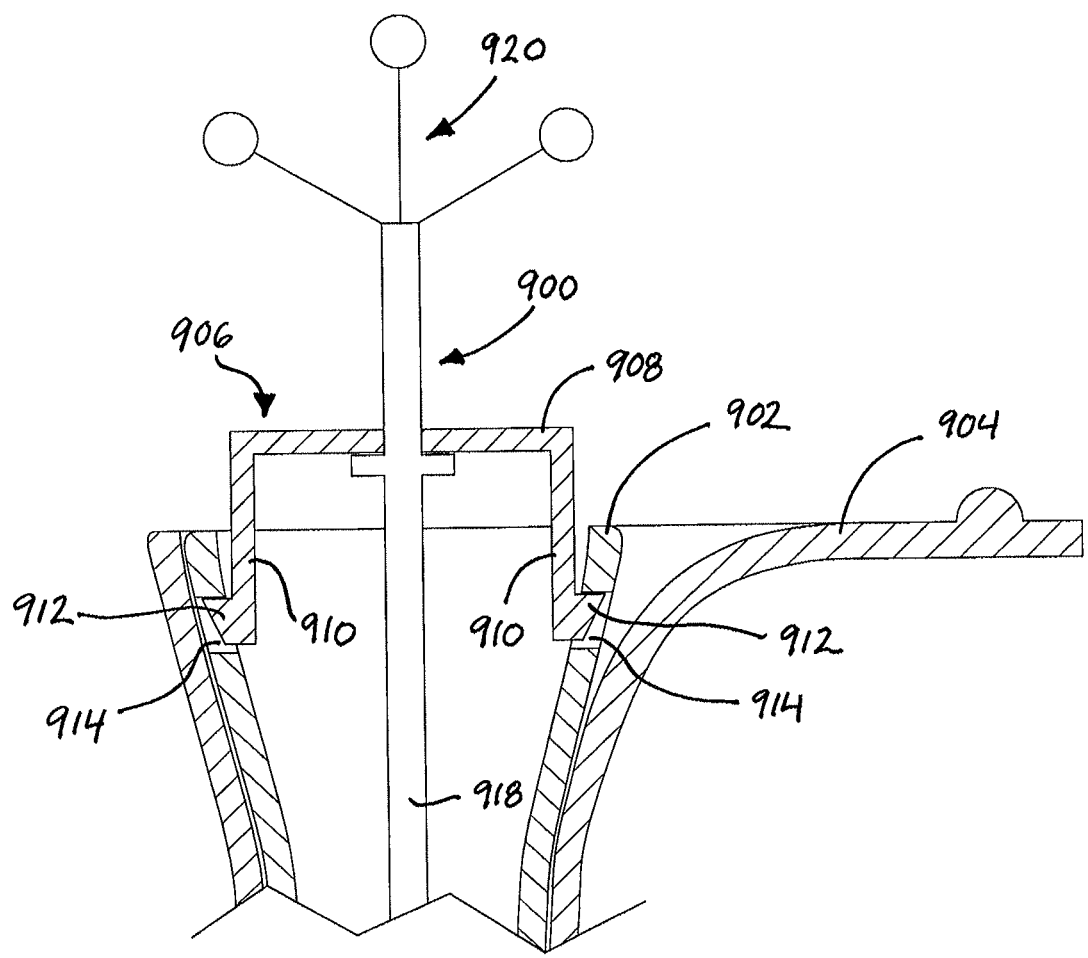
FIG. 9 is a partial cutaway side elevation view of still another exemplary retractor system navigation module and retractor/introducer system.

The foregoing exemplary embodiments have generally illustrated a navigation module that is retained in the introducer either loosely or by friction fitment between parts. FIG. 9 illustrates an example of an embodiment in which a navigation module 900 is connected to an introducer 902 (which is received in a retractor 904) by a mechanical lock 906. The lock 906 comprises an arm 908 having two resilient tabs 910. The tabs 910 each have a protrusion 912 that fits into a corresponding detent 914 on the inner wall of the introducer 902. The arm 906 rests on top of a shelf 916 provided on the shaft 918 of the navigation module 900. The shelf 916, arm 906 and shaft 918 are positioned to hold the tip of the shaft 918 (not shown) in proper registration with the tip of the introducer 902 (not shown). When the lock 906 is engaged over the shelf 906, the shaft 918 is fully inserted into the introducer 902, and a navigation unit 920 at the proximal end of the shaft 918 is properly positioned to navigate. The lock 906 may be released by squeezing the tabs 910 together to disengage the protrusions 912 from the detents 914. It will be appreciated from the foregoing that any other suitable mechanical lock may be used to hold a navigation module in place in an introducer and/or retractor.

It will be appreciated that other mechanisms or parts may be used to hold a navigation module to an introducer/retractor system. For example, the mechanical lock shown in FIG. 9 may be replaced by a different kind of latch system. As another example, the system of FIG. 6 may be modified by removing the O-rings 608, and adding an expanding grip that a surgeon can selectively extend radially from the navigation module shaft 606 to grip the inner walls of the introducer 602.

Figure 10:
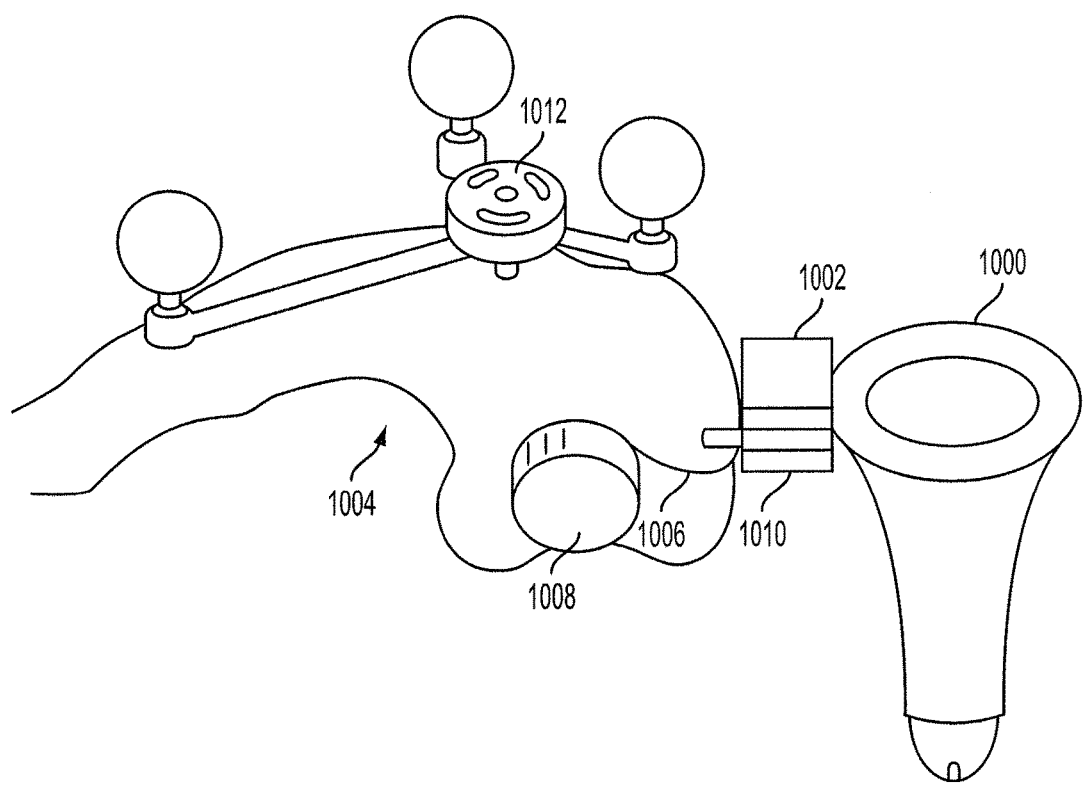
FIG. 10 illustrates an exemplary embodiment of an introducer/retractor system manipulation arm having a navigation unit.

Another exemplary embodiment is illustrated in FIG. 10. In this embodiment, an introducer/retractor system 1000 (which may be held together as a unit by a lock 1002), is connected to a manipulation arm 1004. The arm 1004 includes a clamp 1006 that is tightened onto the introducer/retractor system 1000 by turning a knob 1008 that closes the clamp 1006. Any suitable clamping system may be used for this application. Also, while the shown embodiment shows the clamp 1006 engaged to a handle 1010 that extends from the retractor portion of the introducer/retractor system 1000, the clamp 1006 can engage any other suitable part of the introducer/retractor system 1000. A navigation unit 1012 is connected to the manipulation arm 1004, where it can be used to computer navigate the introducer/retractor system 1000. The navigation unit 1012 preferably is mounted at a location where it does not interfere with visualization into the introducer/retractor system 1000, thereby providing the benefits as described above with respect to the embodiment of FIGS. 7 and 8. It also is preferred for the navigation unit 1012 to be mounted where it can properly work with the rest of the navigation system, such a by being mounted on the top of the arm 1004, or being elevated on a short post. The navigation unit 1012 may be removable or movable to facilitate manipulation of the arm 1004 and viewing through the introducer/retractor system 1000.

Figure 11:
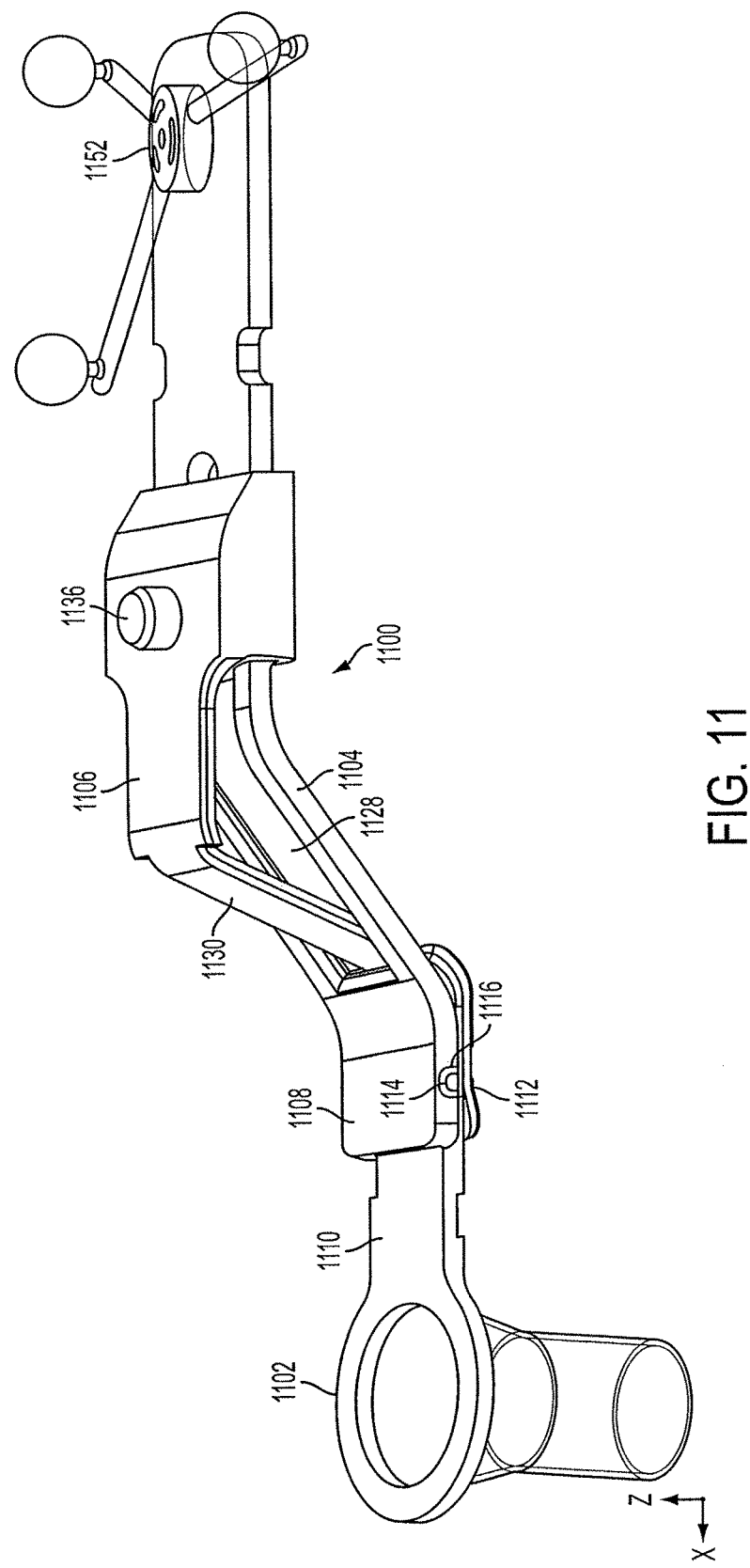
FIG. 11 illustrates another exemplary embodiment of an introducer/retractor system manipulation arm that may be equipped with a navigation unit.

A further embodiment of a manipulator arm is illustrated in FIGS. 11-14. FIG. 11 shows a manipulator arm 1100 that is connected to an elongated elliptical retractor 1102. The retractor 1102 may be constructed as shown in Mangiardi or have other shapes or features. The arm 1100 comprises a first clamp member 1104 and a second clamp member 1106. The first clamp member 1104 has an upper clamp 1108 that fits over a handle 1110 that extends from the retractor 1102. The second clamp member 1106 has a lower clamp 1112 that fits below the retractor handle 1110. The handle 1110 is held between the upper clamp 1108 and lower clamp 1112, and may be retained by a compressive force generated by the clamps 1108, 1112.

The handle 1110 and clamp members 1104, 1106 may include features to help engage them and hold them together. For example, the upper clamp 1108 may include a recess such as groove 1114 that is shaped to receive a corresponding protrusion such as ridge 1116 on the handle 1110. The groove 1114 and ridge 1116 may be straight, but may include a bent portion 1118 (FIG. 13) that ensures that the handle 1110 is positioned at a precise location along the groove 1114. The lower surface of the upper clamp 1108 also may have an indentation 1119 (FIG. 13) with sidewalls 1121 that hold the handle 1110 against rotation. The bent portion 1118 of the groove 1114 and the indentation 1119 and sidewalls 1121 are examples of registration features that hold the retractor 1102 at a fixed location and orientation with respect to the arm 1100. It will be appreciated that in other embodiments the shown registration features may be moved to other locations, transposed, replaced with recesses and grooves having different shapes, or even omitted. For example the groove 1114 may be formed on the handle 1110, and the ridge formed on the lower clamp 1108. In alternative embodiments, the foregoing registration features may be replaced by any arrangement of parts that are shaped to align the retractor 1102 at a particular location and/or orientation with respect to the arm 1100, however, it is not strictly necessary for there to be registration features in all embodiments.

The clamp members 1104, 1106 may be slidable with respect to one another to selectively grip and release the retractor handle 1110. For example, in the shown embodiment, the first clamp member 1104 includes a flat, straight slide portion 1120 (FIG. 13), and the second clamp member 1106 is slidably mounted on the first clamp member 1104 by providing the second clamp member 1106 with a pair of rails 1122 (FIG. 14) that wrap around the slide portion 1120. Each rail 1122 includes one or more inwardly-extending tabs 1124 that are positioned below the slide portion 1120 to capture the slide portion 1120 in place between the rails 1122. If desired, the slide portion 1120 may include one or more cutouts 1126 that are large enough to permit the tabs 1124 to pass through. When it is desired to disengage the first clamp member 1104 from the second clamp member 1106 (such as for cleaning), the second clamp member 1106 may be slid backwards towards the proximal end of the first clamp member 1104 until the tabs 1124 align with the cutouts 1126. At this point, the second clamp member can be lifted vertically off of the first clamp member 1106.

As shown in FIG. 11, the clamp members 1104, 1106 may be interleaved. For example, the first clamp member 1104 may have an open channel 1128 that receives a narrow portion 1130 of the second clamp member 1106. The two parts can be removed by rotating them relative to one another, but in normal use they cannot disengage. This construction is expected to make the arm 1100 relatively compact in the lateral direction, promote part strength, and promote the even application of force across the width of the upper clamp 1108 and lower clamp 1112. The open channel 1128 and narrow portion 1130 may be shaped to permit movement between an engaged position (FIG. 11) and an open position (FIG. 12), and may permit further travel to a release position at which point the tabs 1124 align with the cutouts 1126 to allow the clamp members 1104, 1106 to be disassembled.

Figure 12:
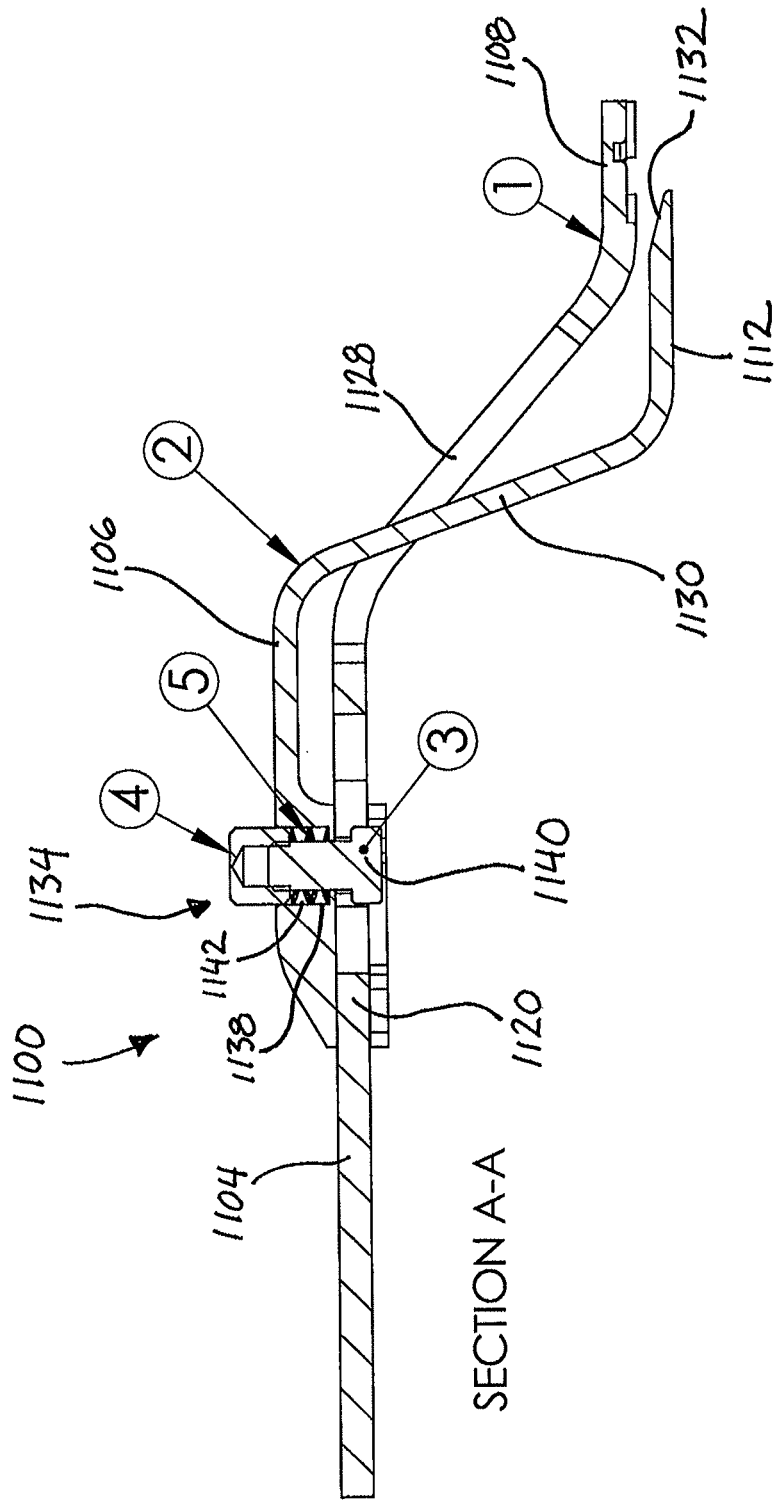
FIG. 12 is a cutaway side view of the manipulation arm of FIG. 11.
Figure 13:
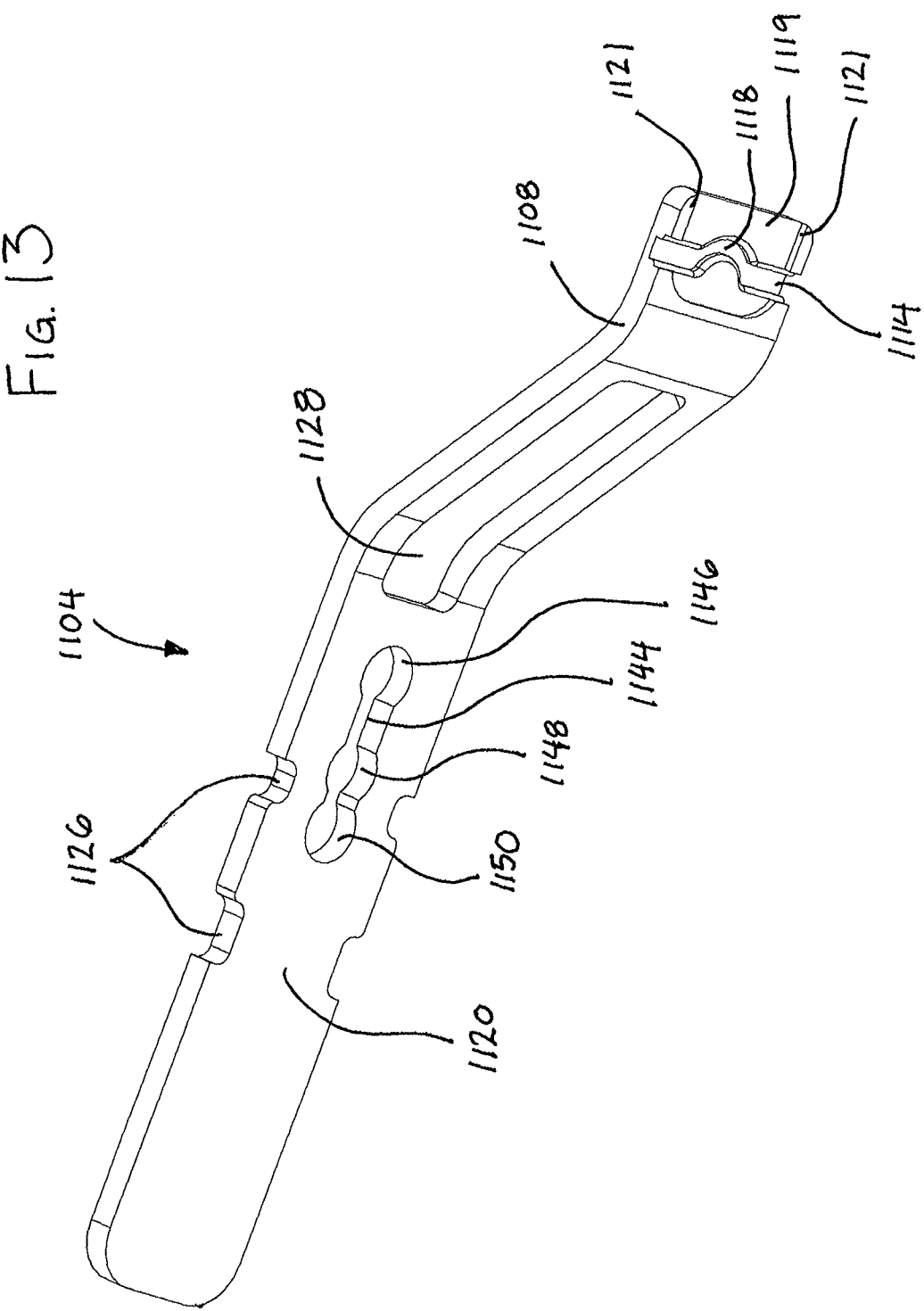
FIG. 13 is an isometric view of a part of the manipulation arm of FIG. 11.
Figure 14:
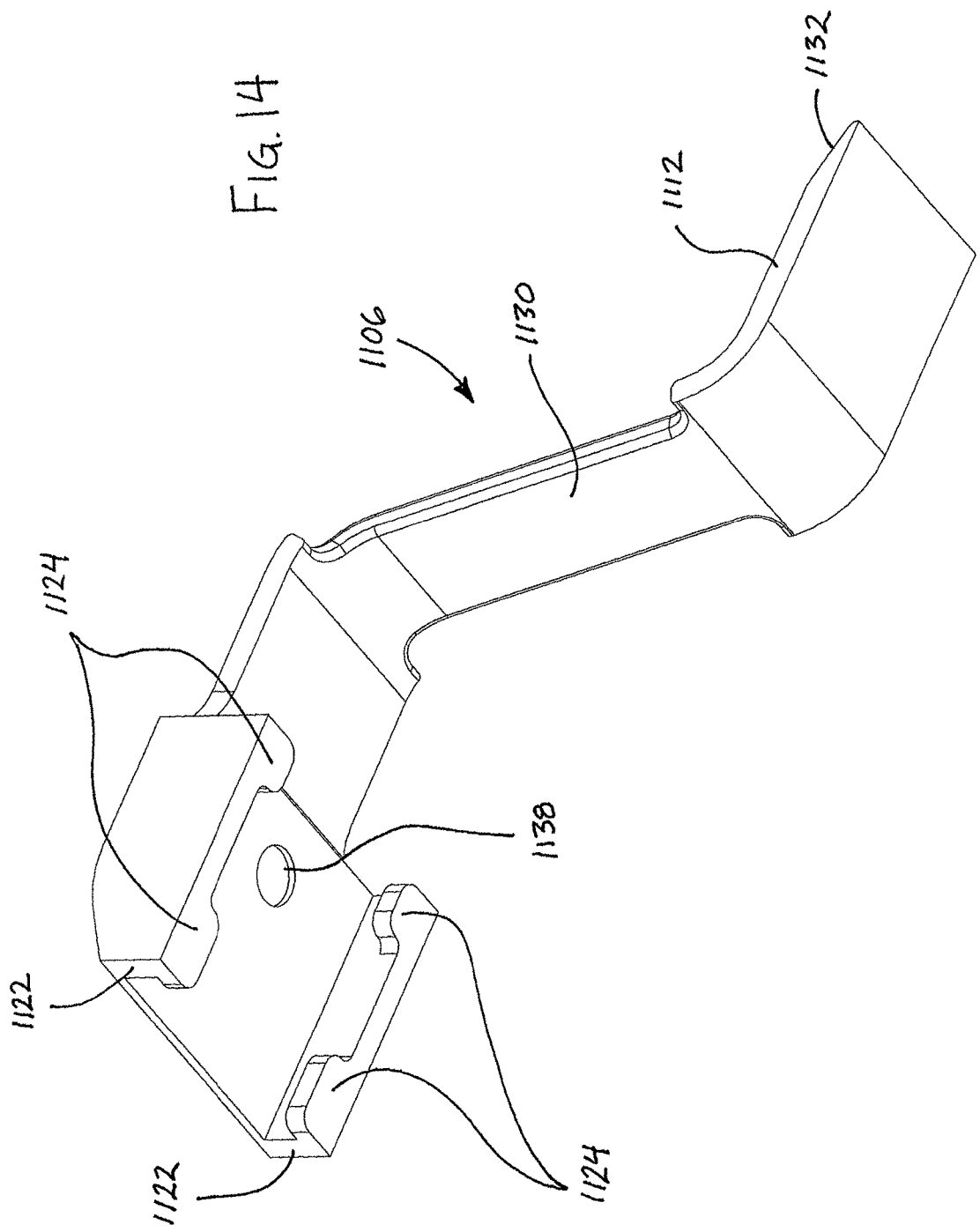
FIG. 14 is an isometric view of another part of the manipulation arm of FIG. 11.

FIG. 12 is a cross-sectional view of the arm 1100 showing the clamp members 1104, 1106 in the open position, and illustrating the general relationship between the parts. As noted above, the arm 1100 may apply a gripping force to hold the retractor 1102. This may be accomplished, for example, by making the vertical clearance between the bottom of the upper clamp 1108 and the top of the lower clamp 1112 less than the vertical height of the handle 1110. Thus, the act of sliding the lower clamp 1112 forward forces the upper clamp 1108 and lower clamp 1112 apart and generates a restoring force that compresses against and grips the handle 1110. To facilitate engagement of the clamps, one or both of the clamps 1108 1112 may include a tapered surface 1132 that slides along the handle 1110 like a wedge to slowly increase the restoring force applied to the handle.

Also, as shown by one example in FIG. 12, the arm 1100 may include a position lock 1134 that selectively holds the first and second clamp members 1104, 1106 at particular locations with respect to one another. In this example, the position lock 134 comprises a button 1136 (also shown in FIG. 11) that extends through a corresponding countersunk hole 1138 (FIG. 14) through the second clamp member 1106. The countersunk hole 1138 has a larger bore adjacent the top surface of the second clamp member 1106, and smaller bore adjacent the lower surface, and is sized so that the button can slide within the larger bore, but cannot pass through the smaller bore. The button 1136 has a threaded bore, and a locking pin 1140 extends up through the smaller portion of the countersunk hole 1138 and into the threaded bore. The locking pin 1140 has a head located below the lower surfaced of the second clamp member 1106. When the locking pin 1140 is threaded into the bore, the pin 1140 and button 1136 are captured on the second clamp member 1106. A spring 1142 is provided in the countersunk hole 1138 to bias the button 1136 and pin 1140 upwards.

When the first and second clamp members 1104, 1106 are connected to one another, the head of the locking pin 1140 may be positioned within one of multiple recesses in a channel 1144 formed in the first clamp member 1104. The channel 1144 may include a first recess 1146 located where the head of the locking pin 1144 rests when the arm 1100 is in the clamped position (FIG. 11), and a second recess 1148 where the head of the locking pin 1144 rests when the arm 1100 is in the open position (FIG. 12). The channel 1144 also may include a third recess 1150 where the head of the locking pin 1140 can rest when the first and second clamp members 1104, 1106 are slid into a release position to disengage them from one another (e.g., when the tabs 1124 are aligned with the cutouts 1126). The channel 1144 itself is narrower than the recesses, but wide enough that the locking pin 1140 can slide along it when it is depressed by pushing down on the button 1136. While this arrangement may be preferred in some embodiments, it is not strictly required in all. Other slide locks or locking mechanisms may be used in other embodiments, if a lock is desired. Where no lock is desired, the first and second clamp members 1104, 1106 may simply be retained by the surgeon's hand or friction.

Referring still to FIG. 11, a navigation unit 1152 may be mounted on the manipulation arm 1100, much like the arm shown in FIG. 10. In this embodiment, it may be useful to locate the navigation unit 1152 remotely from the retractor 1102, to permit a surgeon to grip the arm 1100 between the navigation unit 1152 and the retractor 1102. This location may provide enhanced feel and control during insertion and manipulation, and may inhibit the surgeon's view even less than the embodiments shown previously herein.

Figure 15:
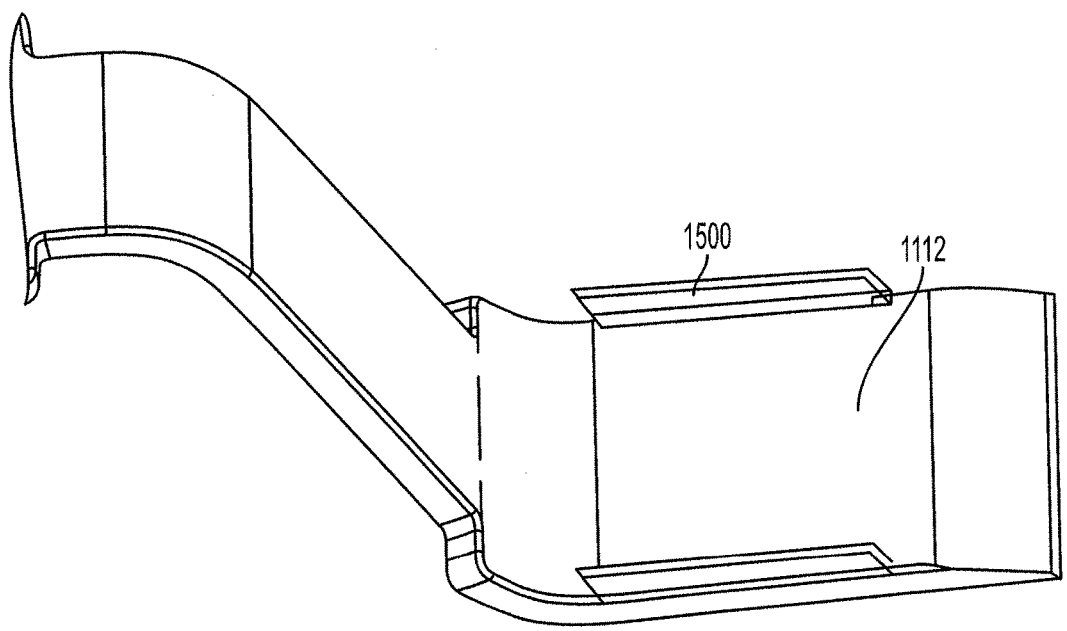
FIG. 15 is an isometric view of a variation of the manipulation arm of FIG. 11.

FIG. 15 shows a variation on the embodiment of FIGS. 11-14. In this embodiment, the lower clamp 1112 is provided with side walls 1500 that fit around either side of the upper clamp 1108. The sidewalls 1500 prevent or inhibit relative movement in the lateral direction between the lower clamp 1112 and the upper clamp 1108, which enhances the stability and strength of the system. In alternative embodiments, the sidewalls could be placed on the upper clamp 1108 to surround the sides of the lower clamp 1112, or replaced by a guide pin or rail located elsewhere (e.g., a guide rail along the centerline of the parts). Other variations will be readily apparent to persons of ordinary skill in the art in view of the present disclosure.

FIGS. 16 and 17 show isometric and partially cutaway side views, respectively, of another embodiment of a manipulation arm 1600. The embodiment is shown in use with an interleaved introducer 1602 and retractor 1604, which may be temporarily connected to one another to form a combined introducer/retractor system. The exemplary introducer 1602 is shown with a navigation module 1604 mounted to it, but this is not required. As with prior embodiments, the manipulation arm 1600 may be provided with a navigation unit that is connected to the arm 1600 itself, and need not be used with navigation system at all (i.e., it may be used solely for visual or manual navigation. The manipulation arm 1600 also may be adapted for use with retractors having different shapes and sizes.

The manipulation arm 1600 includes a handle 1606 and a retractor mount 1608 that may be connected by universal joint, such as a spherical ball joint 1610. The ball joint 1610 permits the retractor mount 1608 to pivot relative to the handle 1606 around one or more axes (three axes or movement capability are provided in the shown embodiment). Any suitable universal or ball joint construction may be used. For example, the ball joint 1610 may comprise a generally spherical ball 1612 that fits in a housing 1614 having a corresponding spherical interior space. The housing 1614 has an opening through which a handle connector 1616 extends to rigidly join the handle 1606 to the ball 1612. The shape and size of the opening and the handle connector 1616 may generally dictate the range of movement of the ball 1612 within the housing 1614. The housing 1614 itself may be formed by two halves that are held together to capture the ball 1612 in place, or it may have sufficient flexibility to allow the ball 1612 to be snapped into the spherical interior space. A lining, such as a low-friction polytetrafluoroethylene (e.g. Teflon™) material, may be provided in the spherical interior space, to hold the ball 1612 firmly. If desired, a clamp (not shown) may be provided to control the friction between the ball 1612 and the housing 1614 or to lock the two together. A clamp may include, for example, a simple threaded screw that threads into the housing 1614 at a location where the screw can be tightened to press the ball 1612 into place within the housing 1614, or a clamp similar to the rotation lock discussed below.

The manipulation arm 1600 also may include a rotating ring mount 1618. The ring mount 1618 includes an inner ring 1620 and an outer ring 1622 that are nested together, with the inner ring 1620 captured in place within a track 1624 on the inner surface of the outer ring 1622. The track 1624 holds the inner ring 1620 in the same plane as the outer ring 1622, but permits the inner ring 1620 to rotate within the plane as the outer ring 1622. A low-friction liner material may be used to facilitate smooth movement between the inner and outer rings 1620, 1622. The inner ring 1620 includes a through-hole 1626 that is shaped to receive the retractor 1604 portion of the introducer/retractor system. The through-hole 1626 may be shaped to conform to the outer wall of the retractor 1604, and may be formed of a high-friction material to help grip and hold the retractor 1604. If desired, a rotation lock 1628 may be provided to increase friction between the inner and outer rings 1620, 1622, or stop relative rotation entirely. For example, the rotation lock 1628 may comprise a threaded screw that can be tightened to open or close a channel 1630 formed in the outer ring 1622, thereby increasing or decreasing the tolerance between the outer ring 1622 and the inner ring 1620.

From the foregoing, it will be seen that the embodiment of FIGS. 16 and 17 provides two unique benefits. First, the universal joint permits the handle to be oriented at various angles relative to the retractor mount, and therefore at various angles to the introducer/retractor system. This allows use where clearance may be an issue, allows the surgeon to hold the device more comfortably, and permits connection to a mounting clamp at different angles. Where a navigation unit is provided on the handle, this flexibility also may permit the handle to be repositioned to receive a navigation signal (although movement mid-surgery may require recalibration of the navigation unit to continue tracking the relevant parts of the introducer/retractor system). The rotating ring mount also enhances the flexibility of the device, by letting the surgeon rotate the introducer/retractor system with one hand, while it is simultaneously being held by the handle. This arrangement is particularly helpful where the surgeon is holding the handle (as opposed to it being mounted by a fixed a clamp), and where the introducer/retractor system is oval instead of round. For oval retractors, rotation may give enhanced 360° viewing and possibly other benefits.

As noted above, any number of navigation systems may be used with embodiments of the invention. Such devices typically operate by associating a navigation unit with a point in space (the "navigation point"). In more sophisticated systems, the navigation unit may be associated with a multitude of points or geometric shapes. For example, a stylet-type navigation module may associate a navigation unit (such as a series of reflective balls) at one end of the stylet with a single navigation point at the other end of the stylet, and it may further associated the navigation unit with the full shape of the stylet. When the computer detects the location and orientation of the navigation unit, it can calculate the location of the navigation point, or even the entire stylet. In the foregoing embodiments, it may be necessary to program the computer navigation system to associate the navigation unit with a navigation point or points on the introducer and/or retractor, or with some other point as desired. For example, in the embodiment of FIGS. 7 and 8, the navigation module 708 may be pre-programmed to associate the location of the navigation unit 710 with the location of the tip 714 of the shaft 706. In this case, it may be necessary or desirable to reprogram this particular navigation module 708 to associate the location of the navigation unit 710 with the location of the tip 716 of the introducer or with other points. If that is the case, then it may be further necessary to prevent the navigation module 708 from rotating relative to the introducer 702, as such rotation might move the location of the virtual navigation point, for example, rotating the navigation module 180 degrees might relocate the associated navigation point to a location 718 that is offset 180 degrees about the axis of the shaft 706 from the tip 716 of the introducer 702.

Such concerns may not be present in devices such as the one shown in FIGS. 2 through 6 and 9, because the tip of the introducer in each of those embodiments is located along the axis of the navigation module. In those cases, however, it may still be necessary or desirable to reprogram the navigation module to account for any difference in distance from the tip of the introducer to the tip of the navigation module. To even further reduce the need to reprogram a pre-existing navigation module such as a navigation stylet, the introducer may be shaped to receive the tip of the navigation stylet at the distal end or tip opening of the introducer, so that no reprogramming is required. For example, the tip opening may have a conical shape to receive a conical navigation stylet tip.

The foregoing considerations generally relate to navigation modules that have a pre-programmed virtual association point. Some navigation units, such as the unit shown in FIG. 10, may not be pre-programmed. Such units may be affixed to the introducer/retractor and programmed on a case-by-case basis with any necessary offset to locate the desired navigation point or points with the orientation and location of the navigation unit. Such programming may be accomplished, for example, by attaching the introducer/retractor system 1000 and navigation unit 1012 to the manipulation arm 1004, locating the tip of the introducer at a known location, and registering the position of the navigation unit 1012 while the introducer is so positioned, to thereby associate the location of the navigation unit 1012 with that known location. Thereafter, wherever the assembly is moved, the navigation system will register the location of the navigation unit 1012 with the position of the tip of the introducer (assuming the parts are not moved relative to one another). Also, while the foregoing examples may use the tip of the introducer as a navigation point, this is not necessary in all cases.

It is also noted that various foregoing embodiments are shown being used in relation with an introducer portion of a combined nested introducer/retractor system. However, the inventors further envision that a navigation module such as described above could be adapted to fit into a retractor that does not have an introducer. FIG. 11 provides one such example. This arrangement may be useful to continue to navigate a retractor after it has been inserted into the patient and the introducer has been removed. Such an embodiment also may be useful to monitor the location of navigation points on the retractor to track any movement that might occur during the course of an operation. A navigation system may be programmed to raise an alarm if the retractor moves by an excessive amount or towards a predetermined prohibited location.

It is also envisioned that a navigation system may be programmed to associate with two different points, such as the distal tip of the introducer and the distal end of the retractor. During introduction, the navigation system can correlate the position of the navigation unit with the tip of the introducer. Once the introducer is removed, the navigation system can then be switched to correlate the position of the navigation unit with the distal end of the retractor. Other associations may also be used, as will be appreciated to persons of ordinary skill in the art in view of the present disclosure.

It is also envisioned that the navigation module in the foregoing embodiments or other embodiments may, itself, be used as a handle to physically manipulate the introducer/retractor system. For example, the navigation module shaft 606 in FIG. 6 may include a manipulation arm that connects directly to the shaft. In such a case, the navigation module should be fastened to the introducer or retractor with sufficient retention force to ensure reliable movement together as a unit under the forces being applied to the navigation module. If the retaining force generated by the O-rings in FIG. 6, for example, is not sufficient, a supplemental lock may be provided to hold the navigation module to the introducer or retractor. For example, the top of the shaft 606 may be connected to the top of the introducer 602 by threads or other mechanisms to enhance the connection between the parts.

In all of the foregoing embodiments, the navigation module, manipulation arm, tip closure member or other features may be made of materials that can either be disposed of after surgery, or reconditioned for later use. For example stainless steel or other materials that can be sterilized (such as by treatment in an autoclave) may be used to form the shaft of a navigation stylet, or to form the manipulation arms shown in FIGS. 10 and 11. While some parts may be reusable, others may be replaceable. For example, the shaft in the embodiment of FIG. 6 may be provided as a reusable material, and the O-ring seals can be easily removed and replaced if they become worn out or cannot be sterilized. Alternatively, the shaft in the embodiment of FIG. 6 may be disposable, but a cost savings may be realized by making the navigation unit removable from the shaft and reusable.

The embodiments described herein may be used in any suitable way to provide the surgeon with computer-assisted navigation or positional feedback. These embodiments can provide a particular advantage by connecting a navigation system to a delicate tissue (e.g., brain) retractor that gently separates and retracts tissue during installation of the retractor while at the same time converting the retractor into a pointer for a frameless or computer-based navigation system. For example, a navigation system such as described previously herein may be affixed to a combined introducer/retractor system before surgery commences, programmed to track one or more navigation points, and then inserted into the patient using stereotactic or other computer-based navigation. During such use, the navigation module may be periodically removed to provide visual access through the introducer and then replaced if desired. Visual access may be possible even with the navigation module in place, although even in those cases it still may be desirable to remove the navigation module to provide greater visual access or access for surgical instruments. When the introducer and retractor are positioned at the surgery site, the navigation may be removed in some embodiments for the remainder of the surgery, or it may be replaced (either with or without the introducer) periodically to adjustment the location of the retractor using computer guidance. The navigation module may alternatively remain connected to the retractor at all times. The details of these and other methods will be readily apparent to persons of ordinary skill in view of the present disclosure.

An example of a surgical procedure using the foregoing embodiments may include a combination of some or all of a number of steps, which may be reordered or repeated as circumstances warrant or by preference of the surgical team or surgeon. A typical surgical process may begin by analyzing (e.g., by CAT scan or MRI) a patient's physiology to locate, as precisely as possible, a lesion within the brain tissue or other part of the body. Once the lesion's location is identified, the surgeon plans the surgical path to the lesion. The surgical path may be conventional, or may take into consideration the unique properties of a retractor system such as shown in FIG. 1 to access surgical sites that might not otherwise be operable. Once pre-surgical planning is complete, the patient is prepared for surgery, an introducer/retractor assembly is equipped with a navigation system, and the navigation system is programmed to associate with one or more points on an introducer/retractor assembly. In a typical brain surgery, the skull is resected to reveal a portion of the dura, which is cut by a minimal incision size to accommodate the introducer and retractor. The arachnoid, pia mater, grey matter and white matter also may be cut to provide access for the introducer/retractor system, but some of all of these steps may not be necessary in all cases. The introducer/retractor system is then inserted into the brain through the cut in the dura, and advanced forward, using the navigation system to monitor and help make corrections to the path of the introducer/retractor system. As the introducer/retractor system is advanced, the navigation module may be removed periodically to permit visual inspection of the brain tissue through the transparent walls (if provided) of the introducer and/or retractor, to permit suctioning of fluid, to relieve pressure, or to permit further incisions through a small opening (if provided) at the tip of the introducer. The navigation module may then be reinserted into the introducer/retractor, and the assembly advanced further into the brain. (Of course, tissue other than the brain may be the subject of the surgical procedure.) The surgeon may also reposition or further advance the assembly with the navigation module removed. Once the introducer/retractor system is positioned at the approximate location of the lesion, the navigation module may be removed to permit final positioning of the system (if necessary), and the introducer may be removed to provide access to the lesion. Surgical procedures may then be performed through the introducer, as indicated for the particular lesion and patient conditions.

While the preferred embodiment of the invention has been described above, it will be recognized and understood that various modifications may be made therein and the appended claims are intended to cover all such modifications which may fall within the spirit and scope of the invention.

We claim:

1. A delicate tissue retraction system comprising:
   a hollow tubular retractor having a proximal retractor end and a distal retractor end;
   a hollow tubular introducer having a proximal introducer end, a distal introducer end, and an inner passage extending from the distal introducer end to the proximal introducer end, the inner passage being defined by a passage wall and the inner passage having a width dimension that increases in size from a smallest size at the distal introducer end to a largest size at the proximal introducer end, the introducer being configured to be removably installed within the retractor with the proximal introducer end being adjacent the proximal retractor end and the distal introducer end extending beyond the distal retractor end; and
   a navigation module configured to indicate the location of one or more points on at least one of the retractor and the introducer to a navigation system, the navigation module comprising:
      a shaft having a proximal shaft end, a distal shaft end, and a middle shaft portion located between the proximal shaft end and the distal shaft end, and
      a navigation unit mounted to the proximal shaft end, wherein the navigation module is dimensioned to removably install within the introducer with the distal shaft end contained within the introducer, the middle shaft portion spaced from the passage wall, and the navigation unit outside the introducer.

2. The delicate tissue retraction system of claim 1, wherein the distal introducer end comprises a closed tip.

3. The delicate tissue retraction system of claim 1, wherein the inner passage terminates at a tip opening that passes through the distal introducer end.

4. The delicate tissue retraction system of claim 3, wherein the distal shaft end comprises a plug configured to install adjacent the tip opening.

5. The delicate tissue retraction system of claim 1, wherein the width dimension of the inner passage increases in size from the smallest size at the distal introducer end to an intermediate size between the smallest size and the largest size at location that is adjacent the distal retractor end when the introducer is fully installed within the retractor.

6. The delicate tissue retraction system of claim 5, wherein the distal shaft end is proximate to the distal introducer end when the navigation module is fully installed within the introducer.

7. The delicate tissue retraction system of claim 1, wherein the distal shaft end is spaced from the distal introducer end when the navigation module is fully installed within the introducer.

8. The delicate tissue retraction system of claim 1, wherein the middle shaft portion extends along a centerline of the introducer when the navigation module is fully installed within the introducer.

9. The delicate tissue retraction system of claim 1, wherein the middle shaft portion is spaced from the passage wall throughout the inner passage from the proximal introducer end to a location adjacent the distal retractor end when the introducer is fully installed within the retractor and the navigation module is fully installed within the introducer.

10. The delicate tissue retraction system of claim 1, wherein the distal shaft end is proximate to the passage wall, and the middle shaft portion is spaced from the passage wall throughout the introducer when the navigation module is fully installed within the introducer.

11. The delicate tissue retraction system of claim 1, wherein the passage wall generally comprises a tubular structure with a uniform wall thickness.

12. The delicate tissue retraction system of claim 1, wherein the navigation module further comprises at least one structure extending radially from the middle shaft portion and configured to contact to the passage wall when the navigation module is fully installed within the introducer.

13. The delicate tissue retraction system of claim 12, wherein the at least one structure comprises a resilient seal.

14. The delicate tissue retraction system of claim 12, wherein the at least one structure comprises an arm.

15. The delicate tissue retraction system of claim 12, wherein the at least one structure comprises a mechanical lock.

16. The delicate tissue retraction system of claim 15, wherein the mechanical lock comprises one or more flexible members that are configured to be flexed to release the mechanical lock.

17. The delicate tissue retraction system of claim 16, wherein the one or more flexible members comprise one or more resilient tabs configured to selectively engage one or more corresponding openings.

18. The delicate tissue retraction system of claim 17, wherein the one or more resilient tabs are on the one or more flexible members, and the one or more corresponding openings are in the introducer.

19. The delicate tissue retraction system of claim 1, wherein the navigation unit is selectively removable from the shaft.

20. The delicate tissue retraction system of claim 1, wherein the navigation module comprises one or more frictional connectors configured to releasably hold the navigation module within the introducer.

21. The delicate tissue retraction system of claim 1, further comprising one or more mechanical locks configured to releasably hold the introducer within the retractor.

22. The delicate tissue retraction system of claim 1, wherein at least one of the retractor and the introducer comprises a handle configured to engage a positioning system.

23. The delicate tissue retraction system of claim 1, wherein the inner passage comprises a central portion located between the distal introducer end and the proximal introducer end, and the width dimension of the inner passage is generally uniform within the central portion.

24. The delicate tissue retraction system of claim 23, wherein the inner passage further comprises a proximal end portion between the central portion and the proximal introducer end, and the width dimension of the inner passage increases from the central portion to the proximal introducer end.

25. The delicate tissue retraction system of claim 24, wherein the inner passage further comprises a distal end portion between the distal introducer end and the central portion, and the width dimension of the inner passage increases from the distal introducer end to the central portion.

26. The delicate tissue retraction system of claim 23, wherein the inner passage further comprises a distal end portion between the distal introducer end and the central portion, and the width dimension of the inner passage increases from the distal introducer end to the central portion.

27. The delicate tissue retraction system of claim 23, passage wall comprises a continuous tubular structure throughout the central portion.

\* \* \* \* \*